(12) United States Patent
Black et al.

(10) Patent No.: US 10,088,347 B2
(45) Date of Patent: *Oct. 2, 2018

(54) FLOW DATA ACQUISITION AND TELEMETRY PROCESSING SYSTEM

(71) Applicant: SAUDI ARABIAN OIL COMPANY, Dhahran (SA)

(72) Inventors: Michael John Black, Dhahran (SA); Mohamed Nabil Noui-Mehidi, Dhahran (SA); Talha Jamal Ahmad, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/957,388

(22) Filed: Apr. 19, 2018

(65) Prior Publication Data
US 2018/0238725 A1    Aug. 23, 2018

Related U.S. Application Data

(63) Continuation of application No. 14/632,122, filed on Feb. 26, 2015, now Pat. No. 9,989,387, which is a
(Continued)

(51) Int. Cl.
*G06K 9/00*      (2006.01)
*G01N 29/036*   (2006.01)
(Continued)

(52) U.S. Cl.
CPC .................. *G01F 1/66* (2013.01); *G01F 1/74* (2013.01); *G01N 29/036* (2013.01);
(Continued)

(58) Field of Classification Search
None
See application file for complete search history.

(56) References Cited

U.S. PATENT DOCUMENTS 5,354,146 A * 10/1994 O'Konek ............. E01C 23/088
                                                          299/39.2
5,485,743 A     1/1996 Taherian et al.
(Continued)

FOREIGN PATENT DOCUMENTS

EP       2199755 A1    6/2010
EP       2453230 A1    5/2012
(Continued)

OTHER PUBLICATIONS

"Handbook of Multiphase Metering", Norwegian Society for Oil and Gas Measurement/The Norwegian Society of Chartered Technical and Scientific Professionals, (2005).
(Continued)

*Primary Examiner* — Nancy Bitar
(74) *Attorney, Agent, or Firm* — Bracewell LLP; Constance G. Rhebergen; Albert B. Kimball, Jr.

(57) ABSTRACT

Processing electronics provide flow data acquisition and telemetry for multiphase flow tomographic ultrasonic transceiver arrays. The processing electronics forms pulse drive signals to cause a tomographic pulse sequence to be emitted. Selected ones of an array of the ultrasonic transceivers emit ultrasonic energy in the tomographic pulse sequence for travel through the multiphase flow. The selected transmitting transceiver is isolated while transmitting it, and the remaining the transceivers are enabled to receive measures of the emitted pulse is after travel through the multiphase flow.

8 Claims, 16 Drawing Sheets

Related U.S. Application Data continuation-in-part of application No. 14/595,689, filed on Jan. 13, 2015, now Pat. No. 9,424,674.

(60) Provisional application No. 61/973,367, filed on Apr. 1, 2014.

(51) Int. Cl.
    *G01F 1/66*     (2006.01)
    *G01F 1/74*     (2006.01)
    *G01N 29/22*     (2006.01)

(52) U.S. Cl.
    CPC ..... *G01N 29/222* (2013.01); *G01N 2291/017* (2013.01); *G01N 2291/0222* (2013.01); *G01N 2291/0224* (2013.01); *G01N 2291/106* (2013.01)

(56) References Cited

U.S. PATENT DOCUMENTS

| | | | |
|---|---|---|---|
| 5,719,329 A | | 2/1998 | Jepson et al. |
| 5,845,743 A | * | 12/1998 | Dechant ............. E04G 3/20 182/187 |
| 5,929,342 A | * | 7/1999 | Thompson ............. G01F 1/64 73/861.04 |
| 6,354,146 B1 | | 3/2002 | Birchak et al. |
| 6,655,221 B1 | | 12/2003 | Aspelund et al. |
| 6,758,100 B2 | * | 7/2004 | Huang ............. G01F 1/662 73/861.25 |
| 7,706,986 B2 | | 4/2010 | Froehlich et al. |
| 8,360,635 B2 | * | 1/2013 | Huang ............. G01F 1/663 374/137 |
| 8,576,084 B2 | | 11/2013 | Reese et al. |
| 9,031,797 B2 | | 5/2015 | Huang et al. |
| 9,404,781 B2 | | 8/2016 | Black et al. |
| 9,424,674 B2 | | 8/2016 | Black et al. |
| 2002/0011120 A1 | | 1/2002 | Huang |
| 2003/0051558 A1 | | 3/2003 | Melnikov et al. |
| 2006/0266127 A1 | | 11/2006 | Gysling et al. |
| 2008/0163700 A1 | | 7/2008 | Huang |
| 2009/0306911 A1 | | 12/2009 | Gysling |
| 2010/0299088 A1 | | 11/2010 | Huang et al. |
| 2011/0112773 A1 | | 5/2011 | Atkinson |
| 2012/0055239 A1 | | 3/2012 | Sinha |
| 2012/0227473 A1 | | 9/2012 | Sinha |
| 2013/0086994 A1 | | 4/2013 | Noui-Mehidi |
| 2014/0008304 A1 | * | 1/2014 | Jansen ............. B01D 17/12 210/708 |
| 2014/0331783 A1 | | 11/2014 | Xie |
| 2015/0233747 A1 | | 8/2015 | Mitri et al. |
| 2015/0276445 A1 | * | 10/2015 | Black ............. G01F 1/66 73/861.24 |
| 2015/0346129 A1 | | 12/2015 | Kersey |
| 2016/0076926 A1 | | 3/2016 | McCann et al. |
| 2016/0327419 A1 | * | 11/2016 | Hellevang ............. G01F 1/66 |

FOREIGN PATENT DOCUMENTS

| | | |
|---|---|---|
| WO | 02/077635 A2 | 10/2002 |
| WO | 2005031279 A1 | 4/2005 |
| WO | 2007129897 A1 | 11/2007 |
| WO | 2009112834 A1 | 9/2009 |
| WO | 2012087120 A1 | 6/2012 |
| WO | 2013028870 A1 | 2/2013 |

OTHER PUBLICATIONS

Avinash C. Kak, Malcolm Slaney, "Principles of Computerized Tomographic Imaging," IEEE Press, New York, USA (1988), Chaper 3, pp. 49-112.

Ayob, et al. "Ultrasound Processing Circuitry for Ultrasonic Tomography," Proceedings of the International Conference on Man-Machine Systems, 2009.

Bishop, "Pattern Recognition and Machine Learning", Springer, Berlin, Chapter 3.3 Bayesian Linear Regression p. 152-160 (2007).

Bishop, "Pattern Recognition and Machine Learning", Springer, Berlin, Chapter 4.5 Bayesian Logistic Regression p. 217-220 (2007).

Bishop, "Pattern Recognition and Machine Learning", Springer, Berlin, Chapter 8.1 Bayesian Networks p. 360-371 (2007).

Brennen, C.E., "Fundamentals of Multiphase Flows", Cambridge University Press, Chapter 7 Flow Patterns p. 163-195 (2005).

International Search Report and Written Opinion for related PCT application PCT/US/2015/021383 dated Jul. 22, 2015.

International Search Report and Written Opinion for related PCT application PCT/US2015/021371 dated Dec. 14, 2015.

International Search Report and Written Opinion for related PCT application PCT/US2015/021375 dated Jul. 22, 2015.

International Search Report and Written Opinion for related PCT application PCT/US2015/021419 dated Jul. 22, 2015.

International Search Report and Written Opinion for related PCT application PCT/US2015/021437 dated Jul. 22, 2015.

International Search Report and Written Opinion for related PCT application PCT/US2017/037266 dated Aug. 18, 2017.

H. Luo, "A Training Based No-Reference Image Quality Assessment Algorithm," Int. Conf. on Image Proc., 5 (2004) pp. 2973-2976.

Hindi, "A Noise Tolerant Fine Tuning Algorithm for the Naïve Bayesian Learning Algorithm", J. of King Saud Univ.—Comp. and Int. Sci. 26, (2014) pp. 237-246.

L. Sirovich and M. Kirby, "Low-dimensional procedure for the characterization of human faces," J. Opt. Soc. Am A, 4 (1987), pp. 519-524.

M.H.F. Rahiman et al. "Ultrasonic Process Tomographic Imaging Sensor: An Approach Utilising Transceivers Method", Proceedings of the International Conference on Computer and Communication Engineering, 2008.

M.H.F.Rahiman et al. "Design and Modeling of Ultrasonic Tomography for Two-Component High-Acoustic Impedance Mixture," Sensors and Actuators A: Physical, 147 (2008) pp. 409-414.

M.H.F.Rahiman et al. "The Front-End Hardware Design Issue in Ultrasonic Tomography," IEEE Sensors Journal, vol. 10m No. 7 Jul. 2010, pp. 1276-1281.

M.H.F.Rahiman et al. "Ultrasonic Transmission-Mode Tomography Imaging for Liquid/Gas Two Phase Flow," IEEE Sensors Journal, vol. 6, 2006, pp. 1706-1715.

M.Turk and A. Pentland, "Eigenfaces for Face Detection/Recognition" J. Cog. Neuroscience, 3(1) (1991), pp. 71-86.

M. Turk and A. Pentland, "Face Recognition Using Eigenfaces", Proc. IEEE Conf. on Comp. Vision and Patt. Recog., (1991) pp. 586-591.

Murrell, H., "Computer-Aided Tomography", The Mathematical J. V6 (1996), pp. 60-65.

Press, Teukolsky, Vetterling, Filannery, "Numerical Recipes in C: The Art of Scientific Computing", Cambridge University Press, 2nd Edition Chapter 10, p. 394-455 (1992).

Rahiman, et al. "Design and development of ultrasonic process tomography." Ultrasonic Waves. InTech, 2012, (pp. 211-226).

Von Kármán vortex shedding. Encyclopedia of Mathematics. URL:http://www.encyclopediaofmath.org/index.php?title=Von_K%C3%A1rm%C3%A1n_vortex_shedding&oldid=23554.

Wahab, Y. A., et al. "Application of transmission-mode ultrasonic tomography to identify multiphase flow regime." Electrical, Control and Computer Engineering (INECCE), 2011 International Conference on. IEEE, 2011, pp. 119-123.

\* cited by examiner

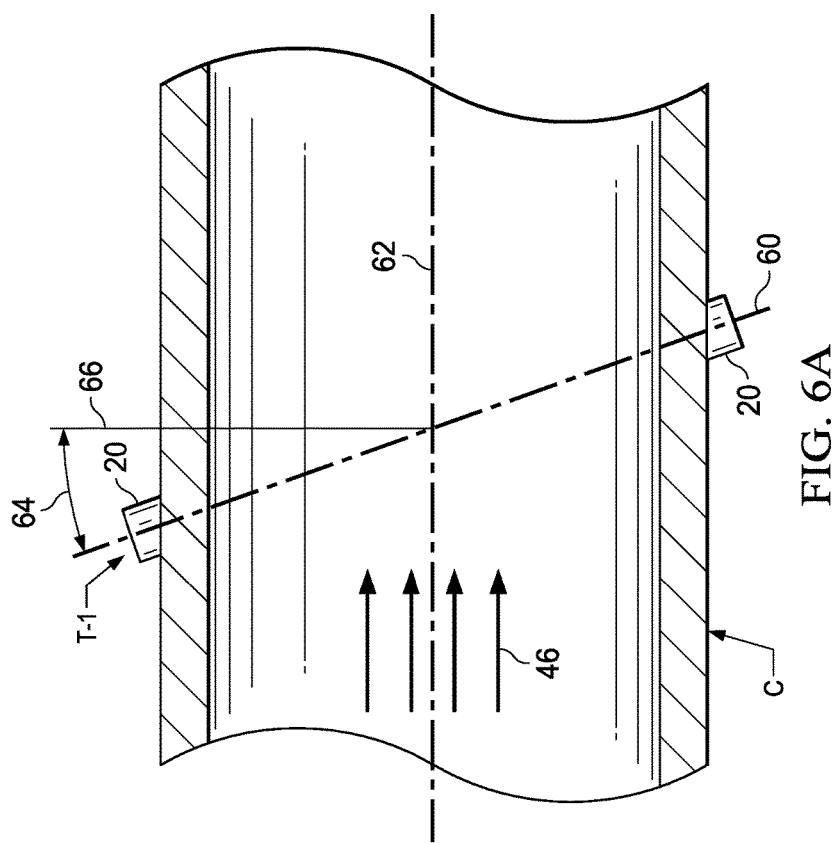

FLOW DATA ACQUISITION AND TELEMETRY PROCESSING SYSTEM

CROSS-REFERENCE TO RELATED APPLICATIONS

This application is a continuation of, and claims priority for, commonly owned, co-pending U.S. patent application Ser. No. 14/632,122 filed Feb. 26, 2015. The present application also claims priority from U.S. Provisional Application No. 61/973,367, filed Apr. 1, 2014, and its related co-pending, commonly owned U.S. patent application Ser. No. 14/595,689, filed Jan. 13, 2015, which have co-pending U.S. patent application Ser. No. 14/632,122.

BACKGROUND OF THE INVENTION

1. Field of the Invention

The present invention relates to sensing flow measures within conduits, and more particularly to sensing flow measures to determine conditions of multiphase flow in conduit.

2. Description of the Related Art

Tomographic imaging of flow tends to focus in general on the imaging of two phases. The technique generally used for two phase flow reconstruction has been based upon what is known as the filtered back projection algorithm. This type of flow reconstruction is described for example by Kak, Avinash C., Slaney, Malcolm *"Principles of Computerized Tomographic Imaging,"* IEEE Press, New York, USA (1988), and Murrell, H. *"Computer-Aided Tomography,"* The Mathematical J. V6 (1996), pp. 60-65.

However, because of the nature of the fluids present in production of oil and gas, it is necessary to form images of three phase flow in conduits involved in hydrocarbon production. Because of the different fluid properties of water (brine), oil and gas it is difficult to address all three sets of fluids simultaneously. In the case of oil-water or water-oil multiphase flows, the medium has been utilized. In the case of liquid-gas or gas-liquid flows (where the liquid is brine or oil or both) an attenuation approach has been utilized. As far as is known, neither method, however, has provided a wholly satisfactory picture of a three phase multiphase flow cross section.

SUMMARY OF THE INVENTION

Briefly, the present invention provides a new and improved apparatus for sensing flow measures within a flow conduit to determine conditions of multiphase flow in the conduit. The apparatus includes an array of a plurality of ultrasonic transceivers mounted about the periphery of the conduit transmitting and receiving energy for travel through the fluid in the conduit. The array of a plurality of ultrasonic transceivers mounted about the periphery of the conduit further receives energy after travel through the fluid in the conduit. The apparatus also includes an input signal forming circuit causing the transceivers to individually emit ultrasonic energy pulses for travel through the multiphase flow in the conduit, and an output signal circuit receiving the ultrasonic energy after travel through the multiphase flow and forming digital data signals from the received ultrasonic energy. The output signal circuit also transfers the formed digital data signals for processing to determine conditions of multiphase flow in the conduit.

BRIEF DESCRIPTION OF THE DRAWINGS

FIG. 6A is a vertical cross-sectional view taken along the longitudinal axis of apportion of the structure shown in FIG. 6.

DETAILED DESCRIPTION OF THE PREFERRED EMBODIMENTS

Figure 1:
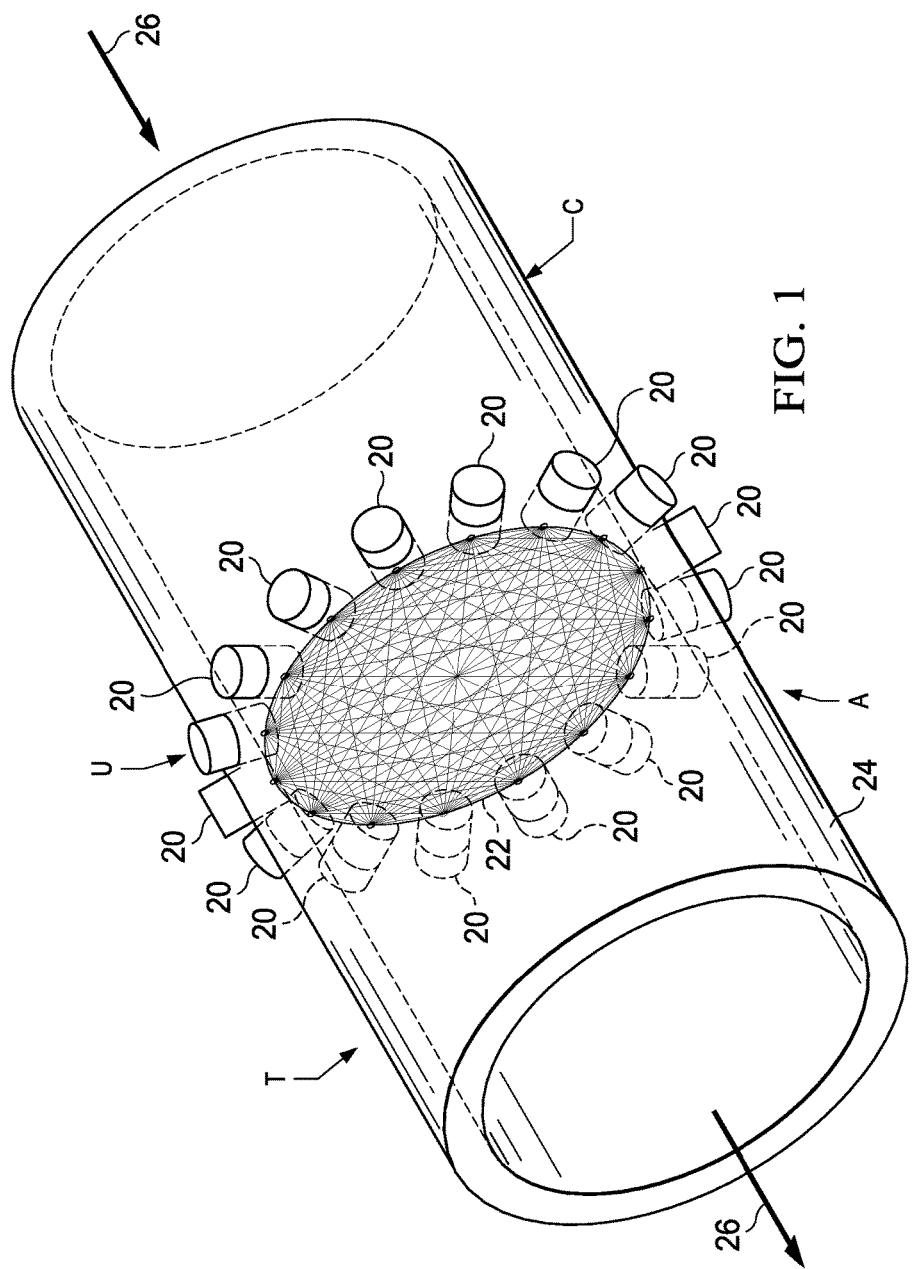
FIG. 1 is an isometric view, partially in schematic diagram form, of an ultrasonic imaging system mounted with a conduit according to the present invention.

Combined Ultrasound Tomography and Vortex Shedding Systems Basic Tomography System By way of background, an introductory explanation of certain commonly owned U.S. Patent Applications of which applicants are named as inventor or co-inventors is provided. FIG. 1 shows the basic configuration of a tomography system T which can be used to measure the cross sectional composition of oil, water and gas in a multiphase flow. This tomography system T is the subject of commonly owned co-pending U.S. patent application Ser. No. 14/595,683 filed Jan. 13, 2015 and having an effective filing date of Apr. 1, 2014. This co-pending application names each of the inventors of the present application as co-inventors. The subject matter of this co-pending application is incorporated herein by reference for all purposes.

The tomographic system T is utilized to form tomographic images of multiphase flow in a flow conduit C, for example in production tubing or surface piping as shown at 24. The multiphase flow enters the tubing C as indicated at 26 and passes through an ultrasonic transceiver array U of the tomographic system T as outlet multiphase flow as also indicated at 26. The tomographic measurement system T in the disclosed embodiment is in the form of the array U of ultrasound transceivers 20 (typically sixteen or more) operating at a fixed measurement frequency, for example 300 kHz. It is also possible to replace the transceivers 20 with transmitter-receiver pairs. However, this acts to minimize the efficient use of space, which could be a concern where there are space limitations as a result of the diameter of production tubing 24 being downhole, where the diameter could be of the order of 3".

The tomographic system T for data acquisition is a component of an apparatus A, which also includes processing electronics E (FIG. 12) and a data processing system D (FIG. 15) to provide output data indicating multiphase-flow metering, as will be set forth. The data processing system D also operates according to related co-pending U.S. patent application Ser. No. 14/595,688 to determine and provide three-phase descriptions of the multiphase mixture based on measurements from the tomographic system T. In this preferred embodiment the three phases are oil, water (brine) and gas.

As described in the previously cited co-pending U.S. patent application Ser. No. 14/595,689, the travel of energy through the fluids in the conduit C occurs over a network of transmission channels so that fluid properties can be measured along individual ones of the transmission channels between a transmitting transceiver 20 and a receiving transceiver 20 of the array as indicated in FIG. 1. The transceivers 20 are mounted in conduit C so that they are closely coupled acoustically to the multiphase flow.

Applicants' related co-pending U.S. patent application Ser. No. 14/595,689 describes how the tomographic system T operates and also geometries and reconstruction techniques relative to the straightforward implementation flow tomography of multiphase flow in the conduit C. A description of alternative reconstruction algorithms is also provided by Avinash C. Kak and Malcolm Slaney, "*Principles of Computerized Tomographic Imaging*," IEEE Press, New York, USA (1988) and H. Murell, "*Computer-Aided Tomography*," The Mathematical J. V6 (1996), pp. 60-65.

Multichannel Dual Frequency Sensor Array

Figure 2:
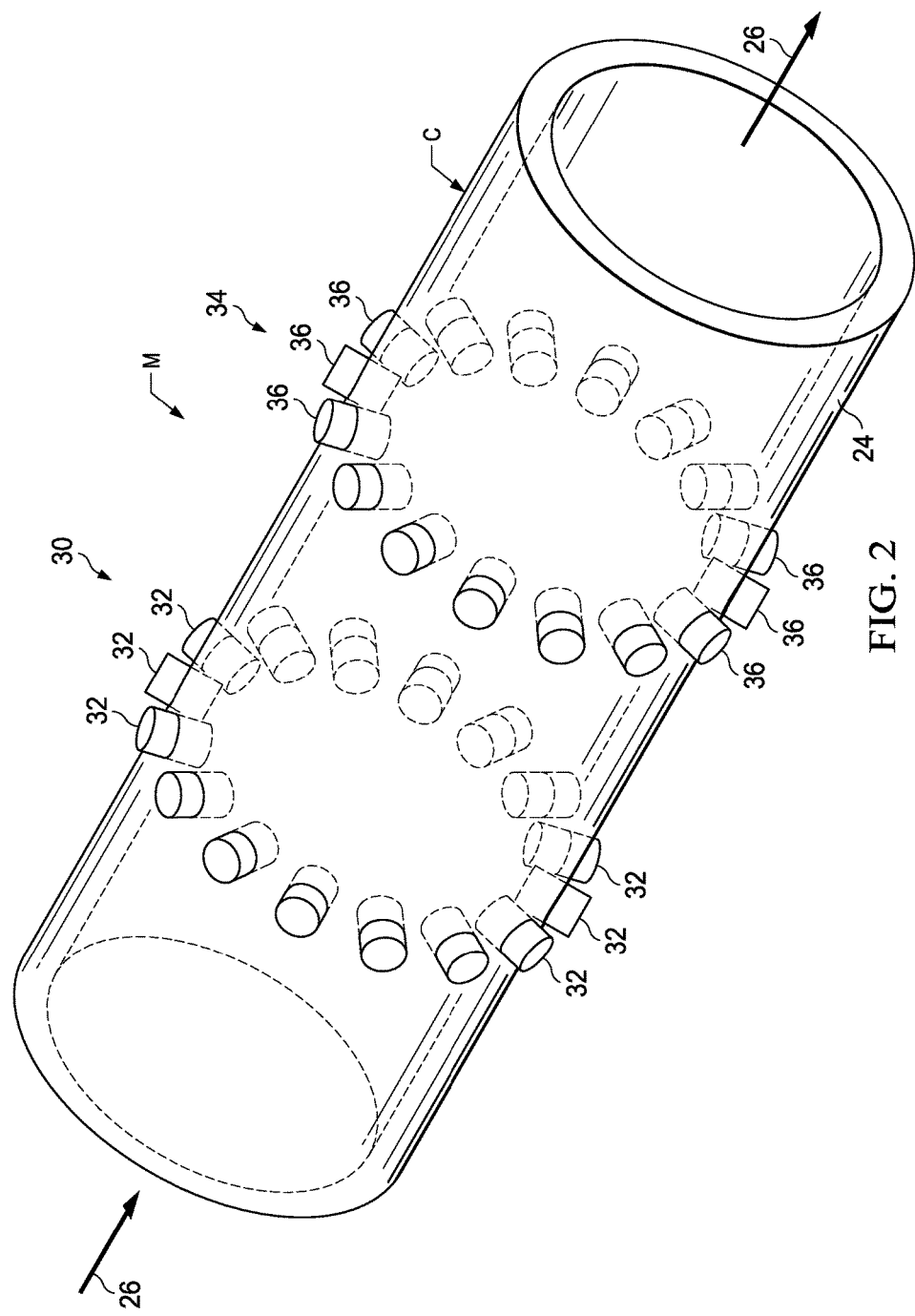
FIG. 2 is an isometric view, partially in schematic diagram form, of a multichannel ultrasonic imaging system mounted with a conduit according to the present invention.

As shown in FIG. 2, a two (or more) channel version data acquisition system M as also described in Applicants' previously cited related co-pending application is shown. The multichannel data acquisition system M may be provided with an example array 30 formed of transceivers 32 deployed circumferentially around the periphery of the tubing 24. The transceivers 32 provide ultrasonic energy at a frequency such as in the range of from 100 to 800 kHz which permits very good resolution, particularly in the measurement of speed of sound in oil-water flows. In the present example, an ultrasonic frequency of 333 kHz is used in transducer array 30. However, energy in these ranges is heavily attenuated by the presence of gas.

Thus, as described in the previously cited related co-pending application, a second array 34 of transceivers 36 is deployed circumferentially around the periphery of the tubing 24. The transceivers 36 like those shown at 34 provide ultrasonic energy, but at a frequency such as in the range of from 20 to 100 kHz which has lower resolution, but which penetrates through gas more effectively resulting in improved images for gas phases. In one example, an ultrasonic frequency of 40 kHz is used in transducer array 34.

Figure 12:
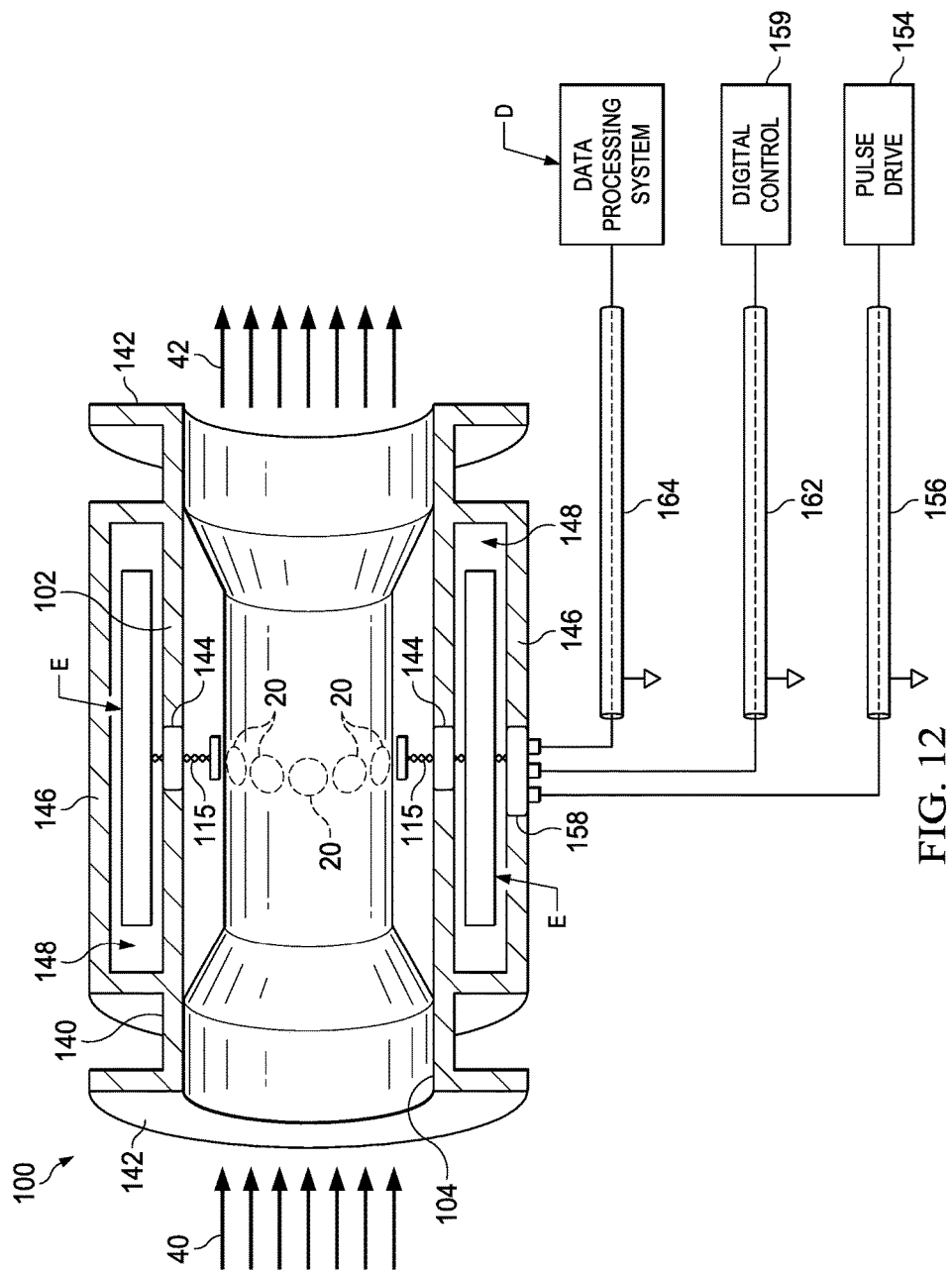
FIG. 12 is a schematic electrical circuit diagram of processing electronics in inline process flow tomography of multiphase flow in accordance with the present invention.

Each range array 30 and 34 thus provides data for independent tomographic processing according to the techniques of FIG. 12 of U.S. patent application Ser. No. 14/595,689. Alternatively, the tomographic processing methodology of FIG. 13 of such co-pending application may, if desired, be directly applied to each of the output images of the sensor arrays 30 and 34 to generate a better image of multiphase flow.

The arrays 30 and 34 can be located in the same plane, or additional arrays of greater or smaller frequencies could be added together to provide a multiple frequency measurement system in order to provide greater measurement performance into regimes where high levels of gas are encountered in the flow. The previously cited commonly owned co-pending application describes processing techniques and methodology used to combine the multiple frequency measurements into a single combined view of the oil, water and gas fraction within the cross sectional area of the conduit. According to the present invention when reference is made to a tomographic array of system in the following description, it should be understood that the tomographic array U may be a single array like that of FIG. 1, as well as a multiple frequency tomographic array M like that shown in FIG. 2.

Vortex Shedding System

Figure 3:
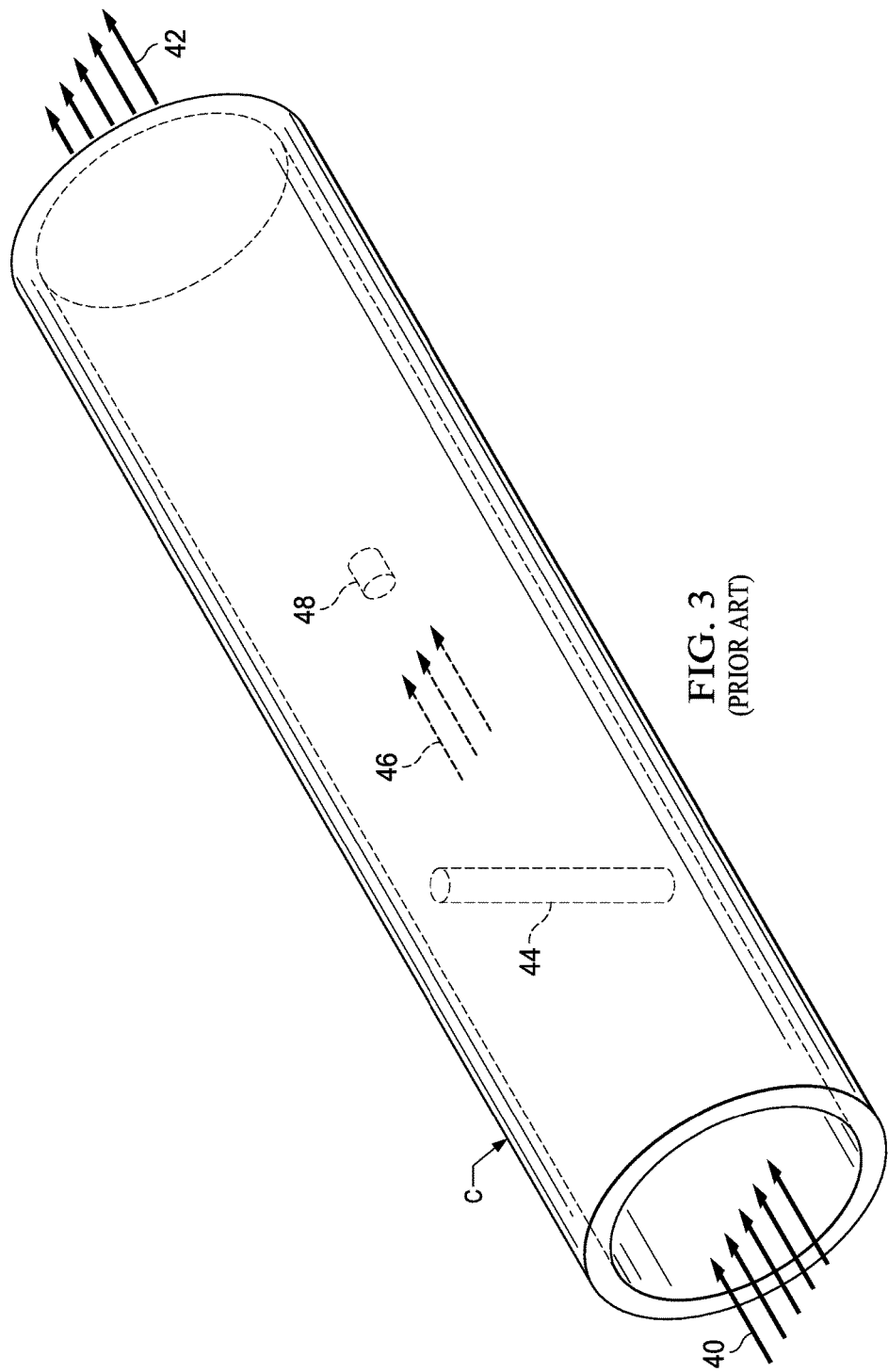
FIG. 3 is an isometric view, partially in schematic diagram form, of a prior art vortex shedding system.

FIG. 3 shows the basic configuration of a conventional, known vortex shedding meter V located in a flow conduit C of the type shown in FIGS. 1 and 2. Inlet flow 40 flows through conduit C and exits as an outlet flow 42. A cylindrical obstruction or bluff body 44 is placed within the flow 46 within the conduit C. The presence of bluff body 44 within the flow generates a von Kármán vortex street with a well-defined frequency downstream of the bluff body 44. The frequency of the von Kármán vortex street is then measured by either a velocity or pressure measuring device 48 placed within the path of the von Kármán vortex street.

The relationship between the vortex street frequency measured in Hz and the flow velocity measure in ms$^{-1}$ is given by the following equation:

$$f = 0.198 \frac{V}{d}\left(1 - \frac{19.7}{\text{Re}}\right) \text{with } 250 < \text{Re} < 2 \times 10^5$$

where f is frequency, V is velocity, d is pipe diameter, and Re is Reynolds number. For sufficiently high Re, the term in the parenthesis tends to be approximately 1, and so the measured frequency varies directly with flow velocity. One of the problems with a vortex shedding meter such as shown in FIG. 3 is that process noise can be high amplitude and also be in the same frequency range as the von Kármán vortex street frequency.

Pulsating Flow Meter

Figure 4:
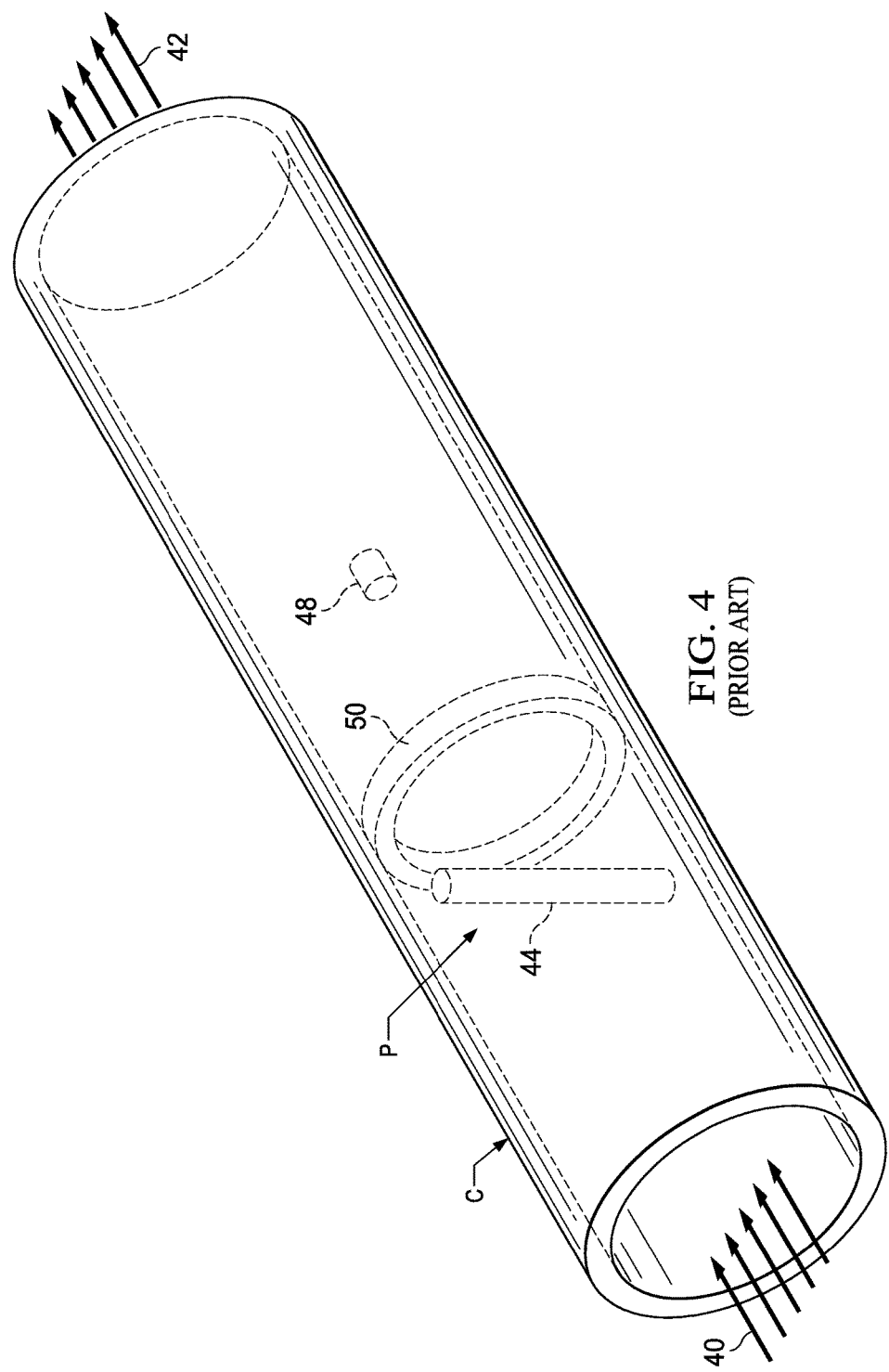
FIG. 4 is an isometric view, partially in schematic diagram form, of a prior art pulsating flow meter system.

FIG. 4 illustrates a pulsating flow meter P which operates according to Published U.S. Patent No. US 2013/0086994 A1 dated Apr. 11, 2013, of which Applicant Noui-Mehidi is named as inventor. In the pulsating flow meter P, like structure to that of the vortex shedding meter bears like reference numerals. As can be seen in FIG. 4, the pulsating flow meter P includes an orifice plate 50. The orifice plate 50 in the pulsating flowmeter P has the effect of lowering frequency and increasing the amplitude of the von Kármán vortex street oscillations. The presence of the orifice plate 50 in pulsating flow meter P improves the performance of the flow metering system relative to the process noise which is normally encountered in a production environment.

The present invention also contemplates pulsating flow meters having vortex shedding systems of other types than the cylindrical bluff body 44 and the orifice plate 48. For example, such vortex shedding systems may take the form of single bluff body systems with a corresponding increase in vortex frequency and decrease in amplitude. A detailed description of the operation of the pulsating flow meter P is provided in previously cited U.S. Published Patent Application No. 2013/0086994 A1.

Multiphase Metering Vortex Shedding and Tomography System

Figure 5:
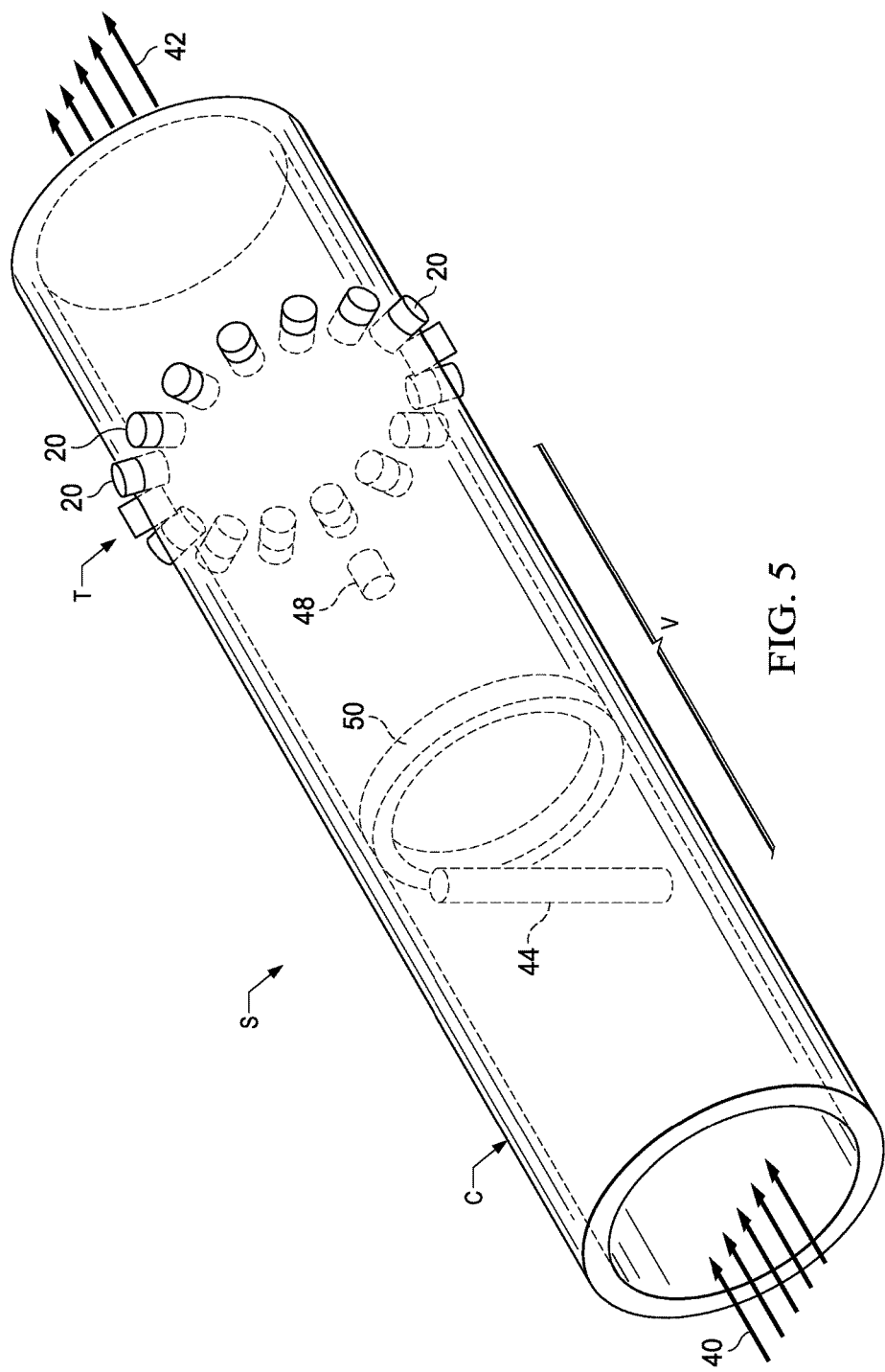
FIG. 5 is an isometric view, partially in schematic diagram form, of a multiphase flow metering vortex shedding system and tomography system according to the present invention.

FIG. 5 is a schematic diagram showing a multiphase metering system S according to the patent invention with a vortex shedding system V of the type described above and a flow tomographic system T, providing full multiphase metering capability. The multiphase metering system S in FIG. 5 receives an inlet multiphase flow 40, flowing through a pipe C, and exiting as outlet flow 42. The flow encounters a cylindrical bluff body 44 of the type described above which generates a von Kármán vortex street which is amplified and pushed down in frequency by the presence of an orifice plate 50 like that previously described. The frequency of the Kármán vortex street is measured by a velocity/pressure measuring device 48. From the measured frequency, the mean velocity of the multiphase can be determined.

The flow then progresses through the tomographic array U which as described above, gathers flow data to determine in the manner of Applicants' co-pending U.S. patent application Ser. No. 14/595,689 the relative amounts or fractions of oil, water and gas contained within the cross sectional area of the conduit C within the array U. The relative fractions so determined, and the mean velocity obtained with the vortex shedding system V are then used in the data processing system D to produce in-situ estimates for the oil, water and gas flows without the need for calibration.

The tomographic array U determines a relative cross sectional fraction of oil, water (or brine) and gas expressed as a percentage of total cross sectional area. Since the total cross sectional area of the tomographic measurement section is defined, these percentages can provide an estimate of the exact cross sectional area of each phase fraction expressed in units of area. For example, if the total cross sectional area is 0.5 meters squared, and the oil cross sectional fraction is 30% then the total cross sectional area of oil is equal to 0.15 meters squared. A similar approach would be applied to the other phase fractions.

Referring back to the equation mentioned above regarding the relation between the vortex street frequency and flow velocity, it can be seen that the measured frequency can be correlated with the flow velocity provided that the gas fraction is relatively small and the Reynolds number of the liquid or liquid mixture is sufficiently high so the term in the brackets tends to a value of 1. With this information, the measured output from the vortex shedding device outputs a frequency which can be matched to an overall flow velocity (no velocity slip between phases is assumed) which can be expressed in units of meters per second. Taking as an example, for an oil and water dominated flow, and according to the diameter of the pipe and the frequency of oscillations, and a computed of velocity of 5 meters per second, the oil cross sectional area of 0.15 meters squared by the velocity give a volumetric flow rate estimate of 0.75 cubic meters per second.

Skew Tomographic Array

Figure 6:
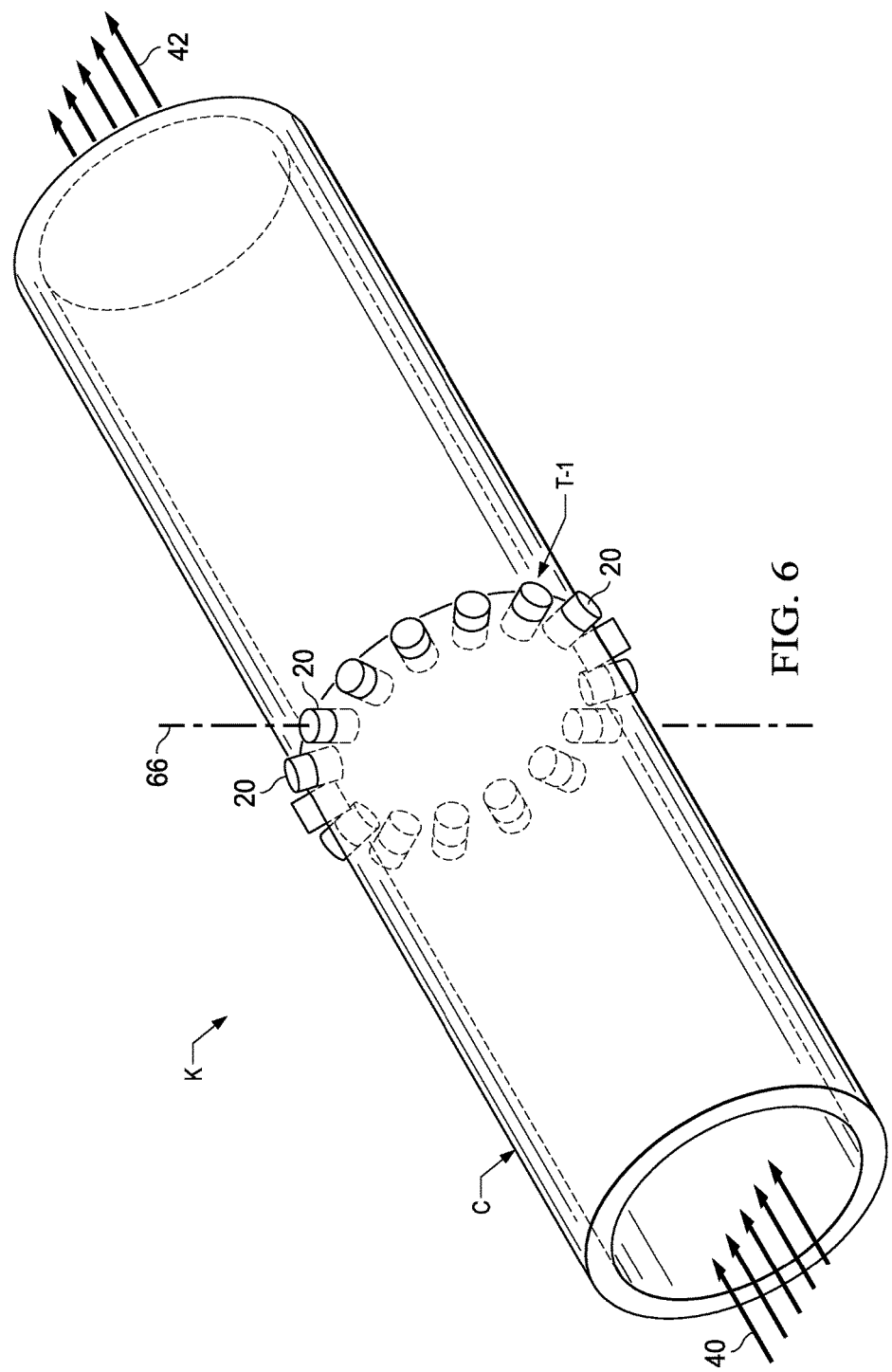
FIG. 6 is an isometric view, partially in schematic diagram form, of a skewed tomographic array of an ultrasonic imaging system according to the present invention.

FIG. 6 shows a schematically skewed tomographic system K according to the present invention which measures multiphase flow provided the system is sensitive enough to measure the Doppler shift caused by the flow velocity. The skewed tomographic system is composed of transceivers 20 of the type described above. The skewed tomographic system K in FIG. 6 as is the case with the tomographic array U obtains data regarding multiphase fluid entering as inlet multiphase flow 40 through conduit or pipe C and exiting as an outlet flow 42. The skewed tomographic array K is inserted or mounted with the conduit C in the manner described above regarding the tomographic system T. The transceivers 20 in the skewed array K are however, located in a plane 60 as shown in FIG. 6A extending transversely to a longitudinal axis 62 of fluid flow in the conduit C. The array K of transceivers 20 as can be seen in FIG. 6A is tilted or skewed at an inclined angle 64 relative a plane 66 extending perpendicularly to the longitudinal axis 62 of fluid flow. The plane as can be seen is that of movement circular cross section of fluid present in conduit C.

In the embodiment shown in FIGS. 6 and 6A, the angle 64 is approximately 15° with respect to the perpendicular cross-section. It should be understood, however, that the array can be skewed at a variety of inclination or tilt up to much higher angles if necessary. The limiting factor is that as the angle 64 increases, the maximum distance that the ultrasound pulses have to travel correspondingly increases. Thus, the transmitted pulses might be limited or distorted either by signal attenuation or by the coherence of the multiphase flow over distance. An angle 64 of about 45° is probably a practical maximum angle for this measurement.

Since the plane of the array K is tilted or skewed, the received signals include a vector component, as the signal which travels between transmitting and receiving transducers 20 includes a component which is in line with the flow in the pipe C in addition to the usual component perpendicular to the flow. Each ultrasonic data measurement of the data gathered for tomographic reconstruction has a known geometry because of the known positions of the transceivers 20. Therefore, the component which is in line with flow can be directly calculated. Any flow velocity thus introduces a Doppler frequency shift on to the received signal. This Doppler frequency which can be measured and back calculated to determine the velocity of the flow.

A source of sound waves with a frequency f which is transmitted across the flow has two components, one at right angles to the flow and a second component in line with the flow. The addition of a flow velocity, v, results in a modification of the speed at which the sound propagates through the fluid medium relative to a stationary receiver. Depending on the relative sizes of the perpendicular and inline components this change in velocity gets larger or smaller: if the sound propagates perpendicular to the flow there is no change to the frequency, if the sound propagates in line with the flow there is a maximum change to the frequency and if the sound propagates at some angle in between these two the frequency is changed according to the size of the sine of the angle between the perpendicular transmission line, and the path between transmitter and receiver. Since the geometry of the transmitter receiver system is known it is possible to correlate any measured frequency difference between source and receiver, matching the frequency difference to an appropriate velocity.

In the case where the pulse is in line with the flow velocity, the flow velocity, v, can be calculated as follows:

$$v = \left(\frac{\Delta f}{f}\right)c$$

where Δf is the measured frequency difference (either positive of negative depending on flow direction), f is the frequency of the source and c is the speed of sound of the medium. It should be noted that in some instances this may require an estimate of the medium properties. This can be extracted from knowledge regarding the relative distributions of fluids with their different respective values of c.

In the case where there is a mixture, according to tomographic back projection theories and models, one may take a weighted average of the various materials' speeds of sounds encountered as the sound wave passes from transmitter to receiver. For example if there is a mixture of 50% oil, with a speed of sound of 1000 meters per second, and of 50% water, with a speed of sound of 1500 meters per second encountered in the transmission path, an assumed c is 1250 meters per second.

As an illustration, two approaches to determine the frequency are set forth. The first is to acquire data at sufficiently high frequency, say ten times the pulse frequency, over a sufficiently long period of time so that the change in frequency can be determined. If the frequency shift is small (only a few Hz) it will be necessary to acquire a sufficiently long train of pulses to accurately determine the frequency. For example, assuming a shift in frequency of 1 Hz, one should expect to have to acquire data over a time period of the order of 1 s. Typically in the disclosed example it is expected to acquire pulse information in a received tomography pulse for on the order of 100 µs, it may be necessary to acquire over a longer period of time requiring many thousands of pulses.

This in some cases may be undesirable. Rather than do this, another method is that of sending a tone through the transmitter over a longer period of time, for example a few seconds of fixed frequency, so that the system has a long enough time to acquire the signal. This requires two modes of pulse drive: one where pulses are driven to generate tomographic information, and a second mode where longer duration pulses are sent to the receiver so that the receiver can acquire sufficiently long enough so that a Fourier transformation of time based data can be performed to generate sufficiently small frequency steps to be able to resolve the anticipated frequency shift.

A second approach to determine frequency is to generate a chirped pulse where the frequency of the transmitter is ramped from some low value to a higher value over a macroscopic period of time. A narrow bandwidth fixed frequency lock in amplifier circuit is included in the processing electronics with a frequency fixed at some value f, and the chirp starts at a frequency well below f−Δf (where Δf is the anticipated flow induced frequency shift). The chirped pulse frequency stops well above f+Δf. If the filter on the lock in is of sufficiently high Q, the received signal occurs at a point where the combination of source frequency and Δf matches the frequency of the lock in amplifier measurement. This occurs at some time after the chirp was started from the receiver.

Knowing the rough time for the pulse to reach the transmitter and the point in time where the pulse was received allows a user to precisely define the frequency shift caused by the flow velocity. This requires a second mode of operation of the topographic array to specially drive the transmitters with a chirped pulse over a period of say 10 s which would be a different mode of operation to that of driving the tomographic array. However, the same transmit-receive hardware can be used, although the addition of a lock in measurement circuit is required.

By amassing many such measurements, the noise on the Doppler shift can be averaged out to provide a lower noise estimate of the flow velocity. In parallel with this, tomographic data sensed by the skewed array K are obtained and processed in the manner of Applicants' previously cited co-pending application to estimate the oil, water and gas fractions within the cross sectional area of the pipe C. The result of the tomographic cross section measurement and the Doppler shift measurement with the present invention from the same array K produces a full multiphase metering capability.

Multiphase Metering Vortex Shedding and Skewed Tomography Array

Figure 7:
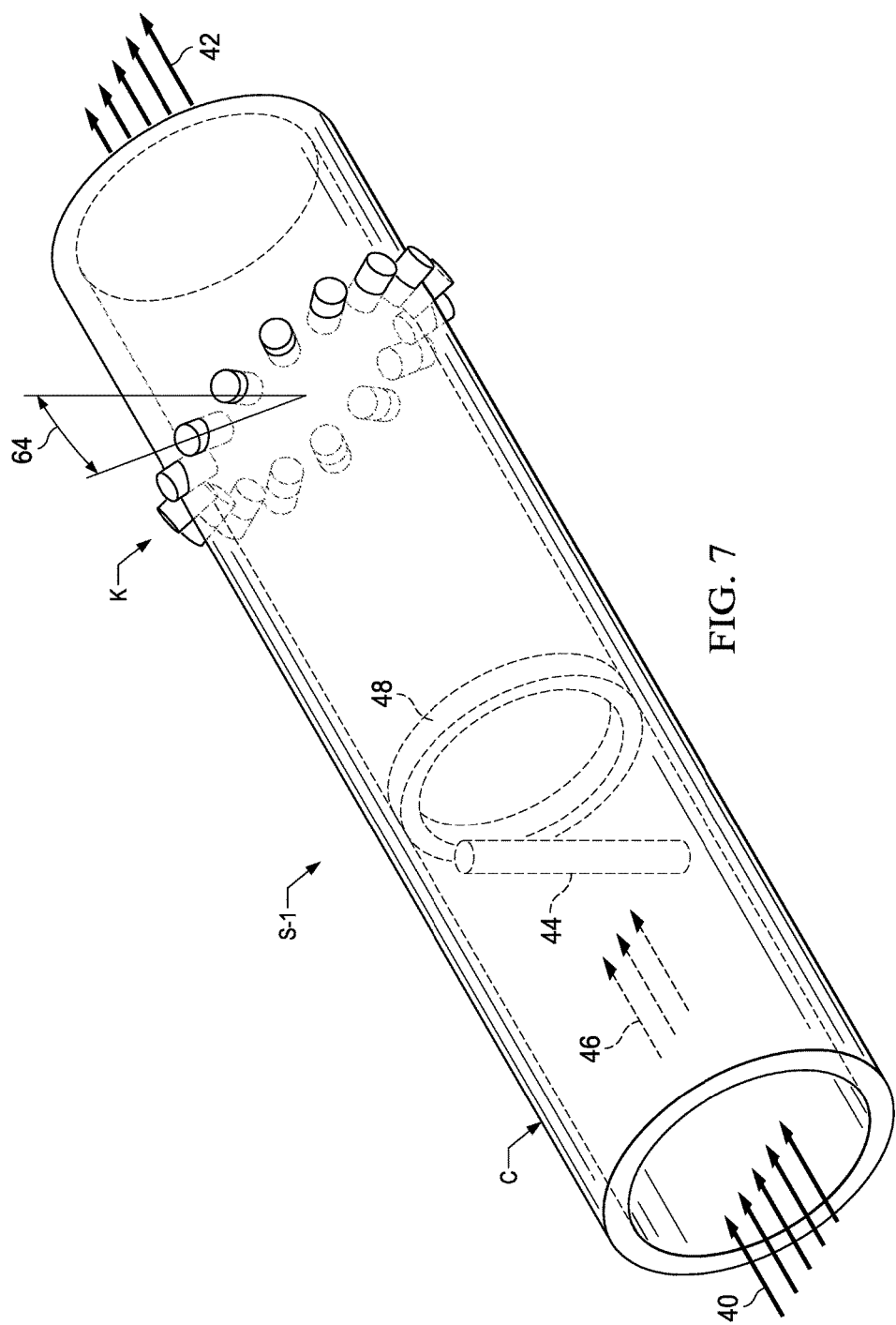
FIG. 7 is an isometric view, partially in schematic diagram form, of a vortex shedding meter with skewed tomographic array of an ultrasonic imaging system to the present invention.

FIG. 7 shows a multiphase metering system S-1 according to the present invention which measures multiphase flow. The metering system S-1 includes a vortex shedding meter V of the type previously described, and a skewed tomographic array K constructed and operating like manner to then array K of FIG. 6. The system S-1 of FIG. 7 receives an inlet multiphase flow 40 which flows as indicated at 46 through pipe C and exits as outlet flow 42. The flow 46 encounters cylindrical bluff body 44 which generates a von Kármán vortex street which is amplified and pushed down in frequency by the presence of orifice plate 48. Unlike FIG. 5, the frequency/velocity measuring device need not be included. With the metering system S-1, the skewed tomographic array K measures flow velocity through Doppler shift as well as oil, water and gas fraction in the manner described above in connection with FIG. 6. Tomographic data sensed by the skewed array K are obtained and processed in the data processing system D in the manner of Applicants' previously cited co-pending application to estimate the oil, water and gas tomography within the cross sectional area of the pipe C.

Although the skewed array K of FIG. 7 provides estimates of the flow velocity itself through Doppler shift, it is likely that a more accurate result can be obtained by measuring the oscillations in flow from the vortex street oscillations. This can be done through a Fourier transform approach during processing filters out any noise except for the well-defined oscillation frequency, whereas straightforward measurement of a direct current or d.c. offset in frequency is subject to white noise fluctuations. Alternatively, the Doppler measurement of velocity by the skewed array K may act as a back-up data measurement to data obtained with the vortex shedding system of bluff body 44 and orifice plate 48. This is of benefit where gas is known to be present in multiphase flow, because the stability of the von Kármán vortex street is degraded by the presence of free gas.

Correlation Tomographic System

Figure 8:
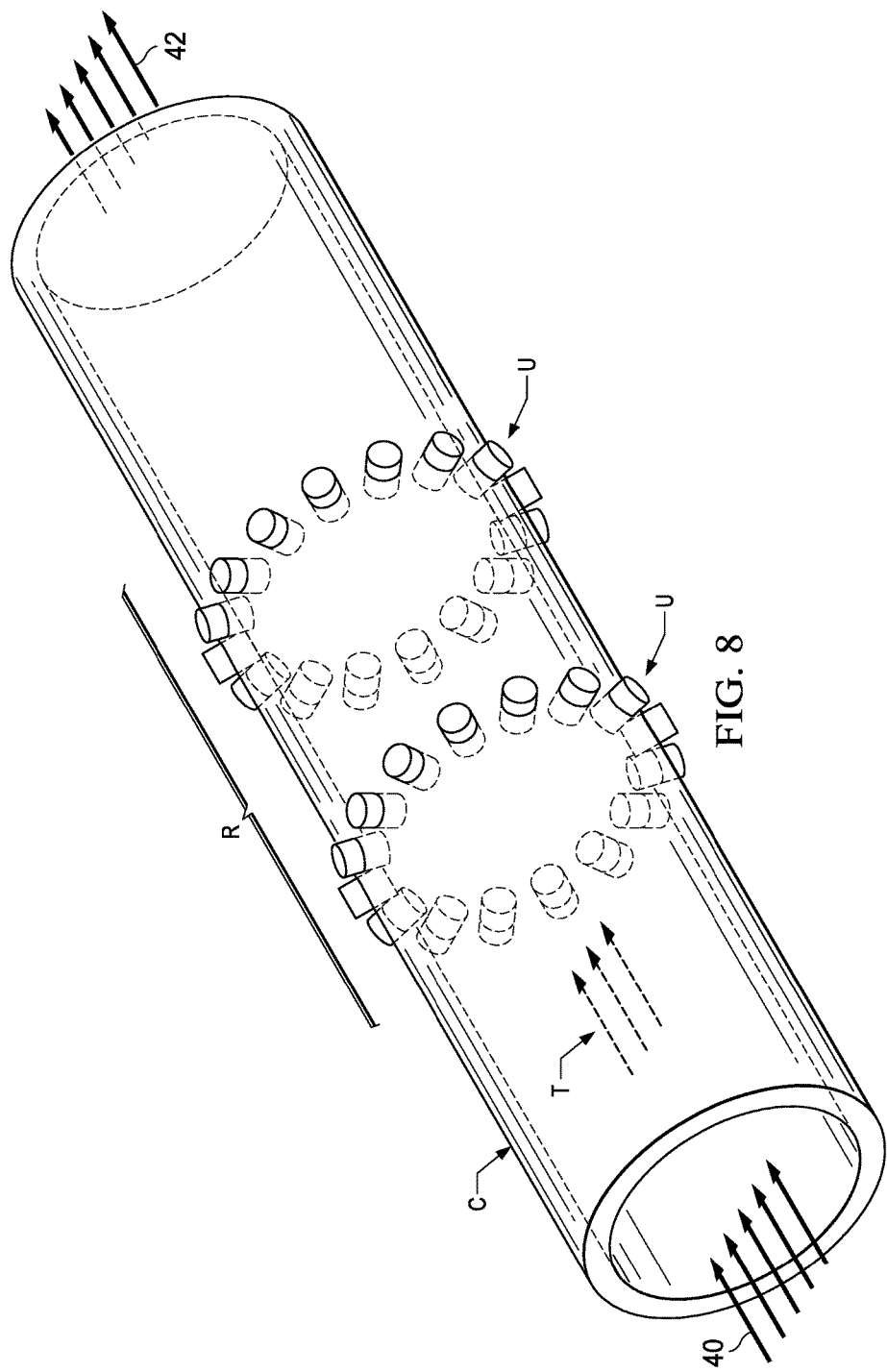
FIG. 8 is an isometric view, partially in schematic diagram form, of correlation tomographic system according to the present invention.

FIG. 8 is a diagram of a correlation tomographic system R according to the present invention, composed of two tomographic arrays U of the type described above regarding FIG. 1 and operating at the same frequency. The tomographic arrays U are spaced at a predetermined distance from each other on the conduit C in the direction of multiphase flow.

Care is taken determining the predetermined spacing distance between the arrays U to ensure that the multiphase flow patterns are coherent across both arrays, so they must be placed relatively close to one another. The precise distance requirement for this is based on interplay between fluid properties and pipe geometry, but a maximum practical distance might be of the order of ~1 m.

As the flow 46 progresses through the pipe C, both tomographic arrays U produce cross sectional images of the flow separated by a known distance, $d_{array}$. As mentioned, this distance is chosen so that flow is coherent across the arrays U. Thus, data defining the cross sectional configuration is measured at the first array U at some time $t_1$. The cross sectional configuration then progresses to be measured by the second array U at some time $t_2 > t_1$ resulting in a travel time measure defined as $t_2 - t_1 = \Delta t$.

In the data processing system D, data from the arrays U are processed in the data processing system D in the manner of Applicants' previously cited co-pending application to estimate the oil, water and gas tomography within the cross sectional area of the pipe C. A memory of data defining the cross sectional configuration of the arrays is retained. Provided the time between tomographic measurements is short relative to $\Delta t$, then $\Delta t$ can be determined in one of the several ways.

One of the ways is for a cross correlation to be performed in the data processing system D between the two sets of sequential cross sectional image captures. Each of the tomographic arrays provides output as described above in the form of an image or dataset based on the measured acoustic responses. In the case of classic tomographic reconstruction, the data is arranged in a 2 dimensional array that is a representation of the cross sectional distribution of fluids that exists within the array. For simplicity it is assumed that this is the output data from each array, and the 2 dimensional image is reconstructed into a 1 dimensional vector. Thus, if there is a N×N 2D image, it is rearranged into a 1 dimensional vector with $N^2$ elements by concatenating each of the rows.

If the output vector from the first array is defined as f and the output vector is defined as g then at a given instant in time there are two vectors. The tomographic system, however, is measuring these vectors at integer time steps. Thus f is defined as a time varying function f[n] where n is an index which increments with each time step in the measurement. Similarly g is defined as g=g[n]. If the flow configuration remains coherent between the two arrays then a time n1>n can be defined where the flow pattern observed upstream at the first array flows downstream and is observed downstream at the second array. Therefore there is a point where f[n]=g [n1].

By calculating the cross correlation:

$$(f*g)[q] = \sum_{m=-\infty}^{m=+\infty} (f[m]*g[m+q])$$

a maximum is obtained in (f*g) [q] when q=n1−n. This is a representation of the time delay represented by the time it takes for the flow pattern measured at the first array to reach the second downstream array. This assumes that the distribution of flow is varying at a sufficiently high levels so that the signal measured at each of the arrays varies with each time step. In the case where there are periods where this does not happen, it is anticipated that flow velocities are to be estimated by interpolating from previously measured values where the flow was sufficiently turbulent to enable sufficient variation in signal to observe a maximum in the cross correlation value.

Each image data set obtained by the arrays U should be the same, except that the downstream or second array U produces the images a time $\Delta t$ after the first array. The time at which the cross-correlation of images indicates them to most closely correspond is a measure of travel time $\Delta t$.

Another way is for a one dimensional cross correlation of the type described above to be performed independently between each of the oil, water and gas fractions determined from the cross sectional images of the multiphase flow. Again the time at which the cross-correlation of images indicates them to most closely correspond is a measure of travel time $\Delta t$. The separate cross correlations produce three different calculations for $\Delta t$ which can be averaged to produce a final travel time value $\Delta t$.

With the known value of $\Delta t$ the fluid velocity can be provided by dividing the separation between the arrays, $d_{array}$, by $\Delta t$. In this way, cross correlating the image data obtained by the spaced arrays U provides an estimate for fluid velocity and also oil, water and gas fraction resulting in estimates for oil, water and gas volumetric flow.

Tomographic data sensed by the arrays U of the correlation array R are obtained and processed in the manner of Applicants' previously cited co-pending application to estimate the oil, water and gas tomography within the cross sectional area of the pipe C.

Multiphase Metering Vortex Shedding with Correlation Tomography Array

Figure 9:
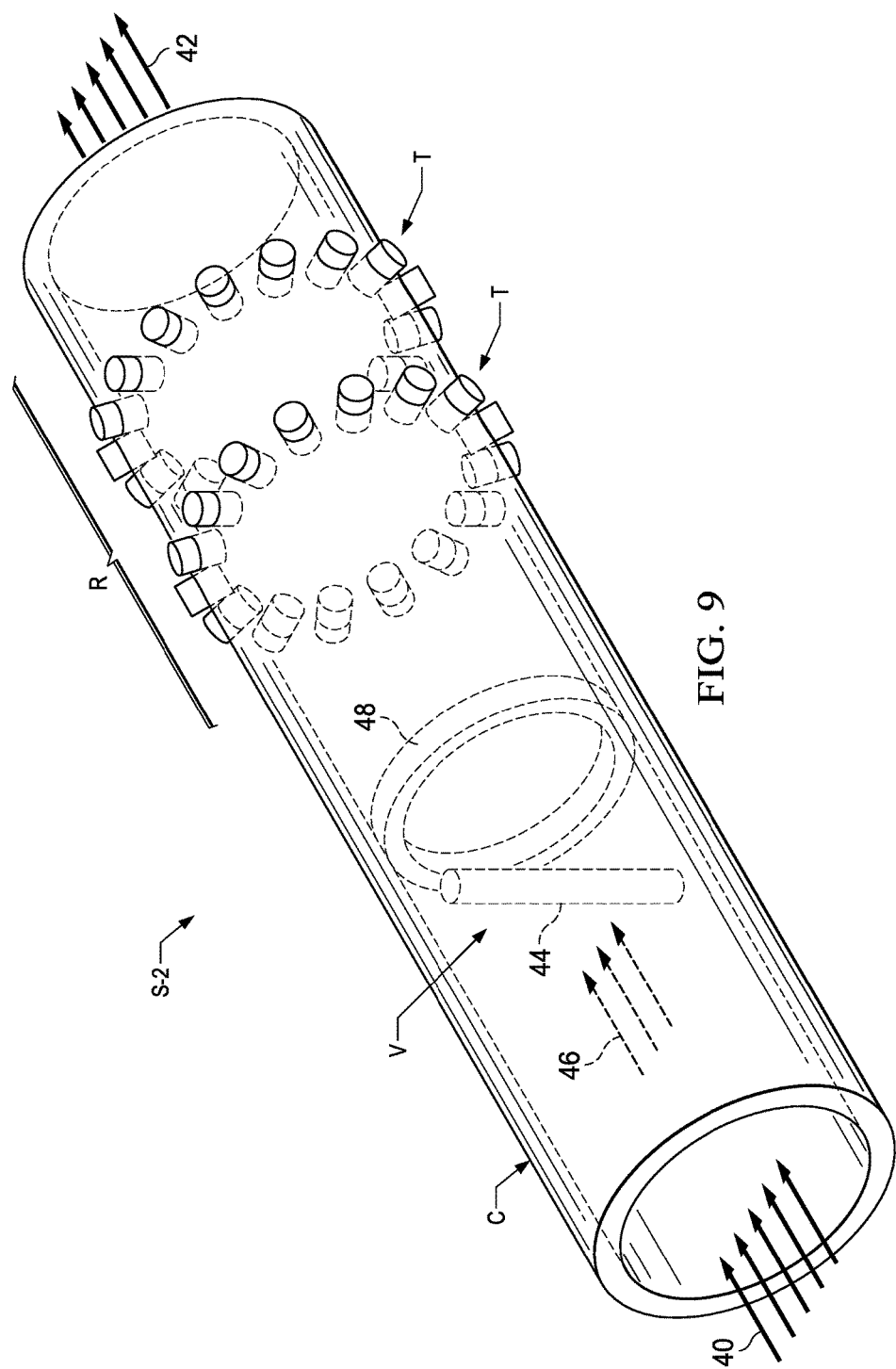
FIG. 9 is an isometric view, partially in schematic diagram form, of a vortex shedding meter with correlation tomographic array according to the present invention.

FIG. 9 shows a multiphase metering system S-2 according to the present invention which measures multiphase flow. The metering system S-2 includes a vortex shedding meter V of the type described above and a correlation tomographic array R like that shown in FIG. 8. The multiphase metering system S-2 receives inlet multiphase flow 40 which proceeds as indicated 46 through pipe C and exits as outlet flow 42. The flow encounters cylindrical bluff body 44 which generates a von Kármán vortex street which is amplified and pushed down in frequency by the presence of the orifice plate 48. In the metering system S-2, correlation tomographic array R measures flow velocity through correlation as well as oil, water and gas fraction. Correlation tomography in the multiphase flow metering system S-2 operates in a like manner to that of the array R shown in FIG. 8 described above to obtain measures of multiphase fluid velocity in the pipe C, and to estimate the oil, water and gas tomography within the cross sectional area of the pipe C.

Although the correlation array may provide an estimate of the flow velocity itself, it is likely that a more accurate result will be obtained by measuring the oscillations in flow from the vortex street oscillations because this can be done through a Fourier transform approach which will filter out any noise except for the well-defined oscillation frequency, whereas straightforward measurement of a direct current or d.c. offset in the correlation measurement will be subject to white noise fluctuations.

From the foregoing it can be seen that according to the present invention, ultrasound tomography arrays and vortex shedding devices provide several advantages over the prior art. The tomographic arrays in conjunction with vortex shedding measure flow velocity and also indicate the cross sectional multiphase fluid composition. Skewed tomographic arrays also provide a capability to measure average flow velocity through Doppler shift of the fluid in addition to indicating cross sectional multiphase fluid composition. Composite arrays of tomographic arrays spaced at a predetermined distance from each other acquire data which with correlation of flow patterns in time permits determination of flow velocity as well as cross sectional multiphase fluid composition.

Skewed tomographic arrays permit measurement of velocity fluctuations downstream of a vortex shedding device where the period and amplitude of the fluctuations is correlated with the mass flow of the fluid. Additionally the skewed tomographic arrays output the relative composition of the multiphase fluid.

Multiple tomographic arrays spaced at a predetermined distance with correlation to determine velocity fluctuations located downstream of a vortex shedding device permit the period and amplitude of the fluctuations to be correlated with the mass flow of the fluid. Additionally, the tomographic arrays output the relative composition of the multiphase fluid.

Figure 10:
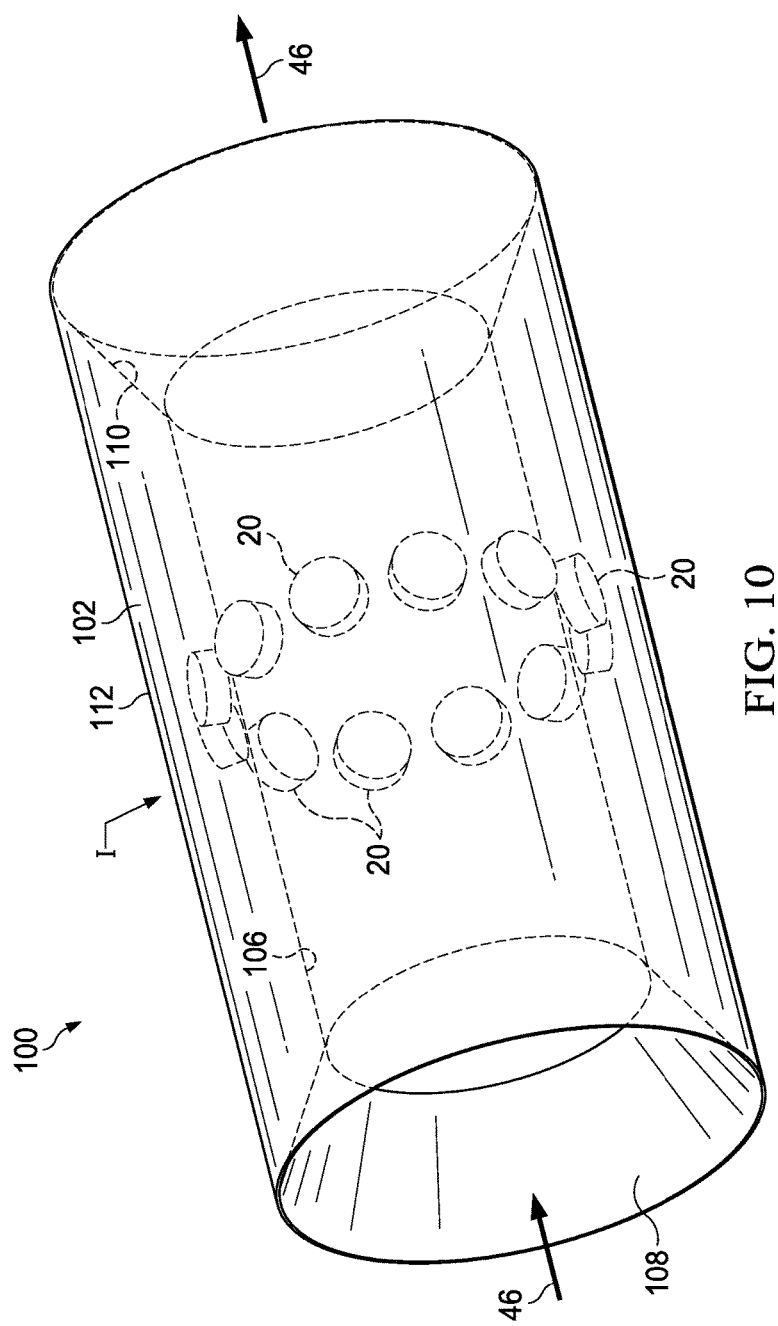
FIGS. 10 and 11 are isometric views, partially in schematic diagram form, of a mounting arrangement for mounting ultrasonic transducers inline in production tubing according to the present invention.

Process Flow Tomographic System Implementation Mounting Inline Ultrasound Transducers A mounting insert I according to the present invention is illustrated in FIG. 10. The mounting insert I positions flow sensing data acquisition transceivers 20 of the arrays of the types described above in the pipe or conduit C to sense multiphase flow conditions. In the embodiment of FIG. 10, an array U is shown, although it should be understood that other arrays could be similarly installed as components of the mounting insert I.

The mounting insert I is in the form of a body or housing 100 of a suitable thermoplastic resin which is fittingly mounted at a desired location within the pipe C to engage and conform along an outer cylindrical wall 102 with an inner cylindrical surface well 104 of the pipe C. The housing 100 has a reduced inner diameter central cylindrical flow passage 106 for travel of the multiphase flow 46. A tapered inlet end 108 and a tapered outlet end 110 are formed on the housing 100 leading to and from the flow passage 106. The taper of the inlet end 108 and the outlet end 110 are selected to prevent fluid turbulence in the multiphase flow through the housing 100. A central sleeve 112 of the housing 100 is formed between the flow passage 106 and the outer surface 102. Fluid data sensing piezoelectric transceivers 20 of the type described above are mounted at circumferentially spaced positions in the central sleeve 112 to transmit ultrasonic energy through a cylindrical inner surface wall 114 for travel through the multiphase fluid in the flow passage 106 for detection by other transceivers 20 in the array U and subsequent processing, as has been described above.

In the embodiment of FIG. 10, dimensions of the thermoplastic housing 100 are an outer diameter equal to the inner diameter of production tubing, about ~3", with an inner diameter hole for flow passage 106 of approximately 2". The total length of the mounting insert I along the length of the conduit C is on the order of about ~6". The piezoelectric elements of the transceivers 20 are piezoelectric stacks which can act selectively as ultrasound transmitters or receivers. The transceivers 20 are electrically connected through twisted pair connections 115 (FIG. 12) which are mounted in sleeve 112 and extend outwardly of the surface 102. The front faces of the piezoelectric elements 20 are mounted close to the inner surface wall 116, for example about 1-2 mm away. The elements 20 and connections 115 can be held in place in a mold as the thermoplastic of the housing 100 is being molded around them. Alternatively, receiving sockets can be drilled from the outside surface 102 of a molded housing body 100, and each element 20 inserted. The sockets are then potted with thermoplastic or epoxy which is allowed to outgas in a vacuum to prevent the presence of bubbles within the housing body 100. The mounting insert when installed in production tubing subject to high ambient pressure. A suitable material in the disclosed embodiment is a thermoplastic polymer resin, such as polyether ether ketone, also known as PEEK.

Figure 11:
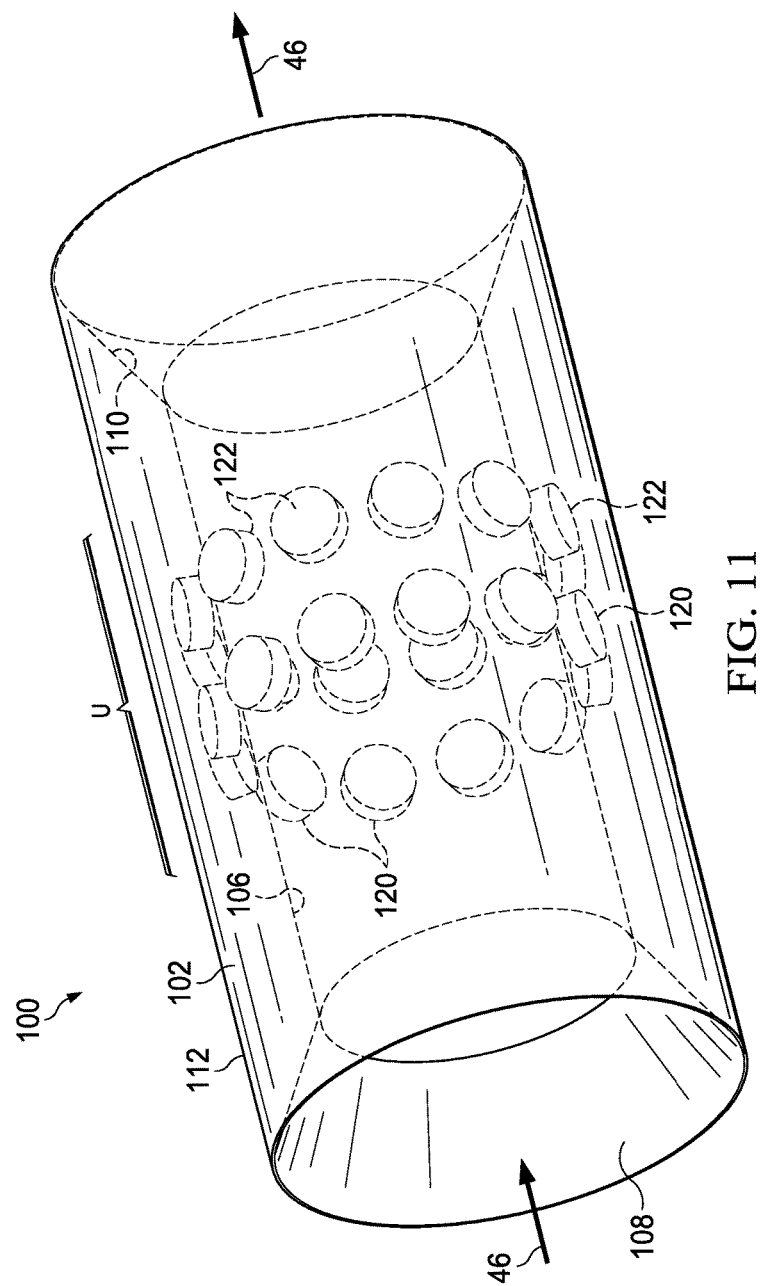

In some production tubing, because of the space constraints in the production environment, it may be necessary to stagger the transceiver elements 20 installed as tomographic arrays to enhance the tomographic resolution. This is shown in FIG. 11. In FIG. 11 the transceiver array U is formed by an additional, closely spaced subarray as indicated at 120 inserted adjacent to a first subarray 122, forming a double array with twice as many piezoelectric transceivers 120. Provided the beam angle of ultrasonic energy emitted is wide enough to cross communicate between the two subarrays 120 and 122, the configuration of FIG. 11 provides additional tomographic elements to thereby increase the resolution to provide good tomographic reconstruction. A rule of thumb for straightforward tomographic reconstruction is that sixteen or more sensors are preferred. However, with processing methodology described in Applicants' previously cited co-pending application, it is now possible to get good results with fewer transceivers, say eight or so.

As can be seen form the foregoing, the mounting insert I of the present invention permits encapsulation of piezoelectric transceiver elements 20 inside a plastic matrix such as PEEK to allow good acoustic coupling and environmental protection of the transceivers. The mounting insert I also provides for wiring arrangements and mechanical structure to minimize the electrical feedthroughs exposed to the harsh temperature and pressure conditions encountered with in line flow metering, with a toroidal space to mount the processing electronics. Further the processing electronics digitize the data sensed in multiple analog channels and send the measured data across a serial digital interface, rather than having multiple analog outputs which could affect the pressure integrity of the pipeline containing the multiphase flow.

Inline Process Flow Tomographic System

FIG. 12 illustrates an apparatus A according to the present invention with the mounting insert I of FIG. 10 in the conduit C, in this embodiment a production fitting 140. As in the embodiments described above, an inlet multiphase flow 40 enters the fitting 140 installed as a component of a production tubing string. The multiphase flow passes as indicated at 46 through the mounting insert (1) and exits as outlet multiphase flow 42. The production fitting 140 has inner diameter of about ~3" close to that of the remainder of the production tubing string. The fitting 140 is connected in the production string to the other production tubing pipes by a connection system which in the embodiment shown takes the form of a conventional ISO flange 142. It should be understood that other forms of connection system compatible with surface or downhole production tubing may also be used, if desired, to connect the fitting 140 in the production string.

The thermoplastic mounting insert I of FIG. 10 containing the array of piezoelectric transceiver elements 20 is mounted firmly inside the fitting 140. Twisted pair connection wires 115 extend from each of the transceiver elements 20 and are electrically connect the transceivers 20 through a high integrity feedthrough 144 to the processing electronic circuit E of the apparatus A. The feedthrough 144 protects the electrical components against fluid pressure and temperature, and maintains pressure integrity. A second cylindrical outer tubing wall 146 is formed on the fitting 140 between the flange connections 142, providing a toroidal cavity 148 for receiving the processing electronic circuit E. After installation of the processing electronic circuit E, the cavity 148 is backfilled with outgassed epoxy for pressure compensation.

Figure 13:
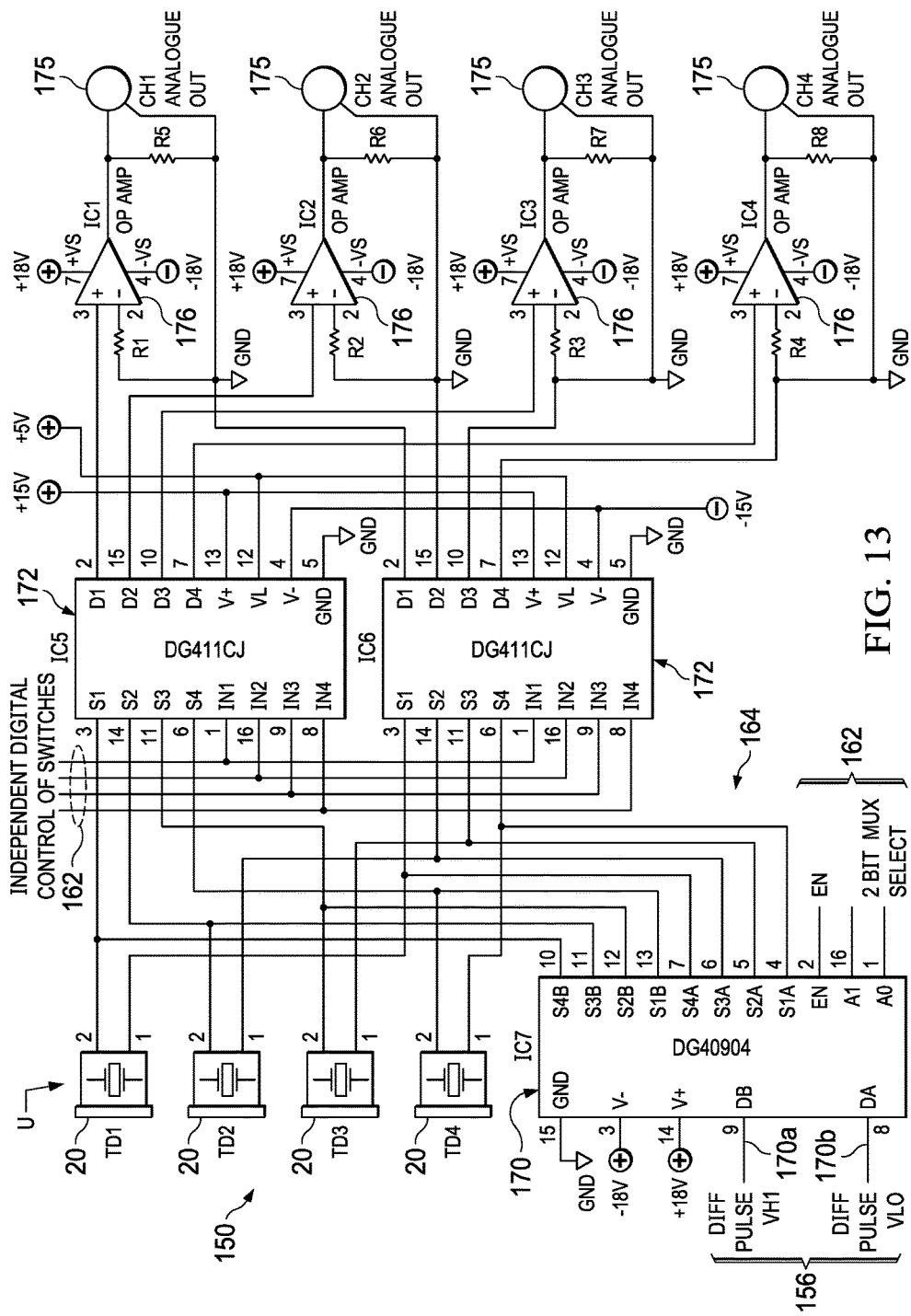
FIG. 13 is a schematic electrical circuit diagram of a portion of the processing electronics of FIG. 12.
Figure 14:
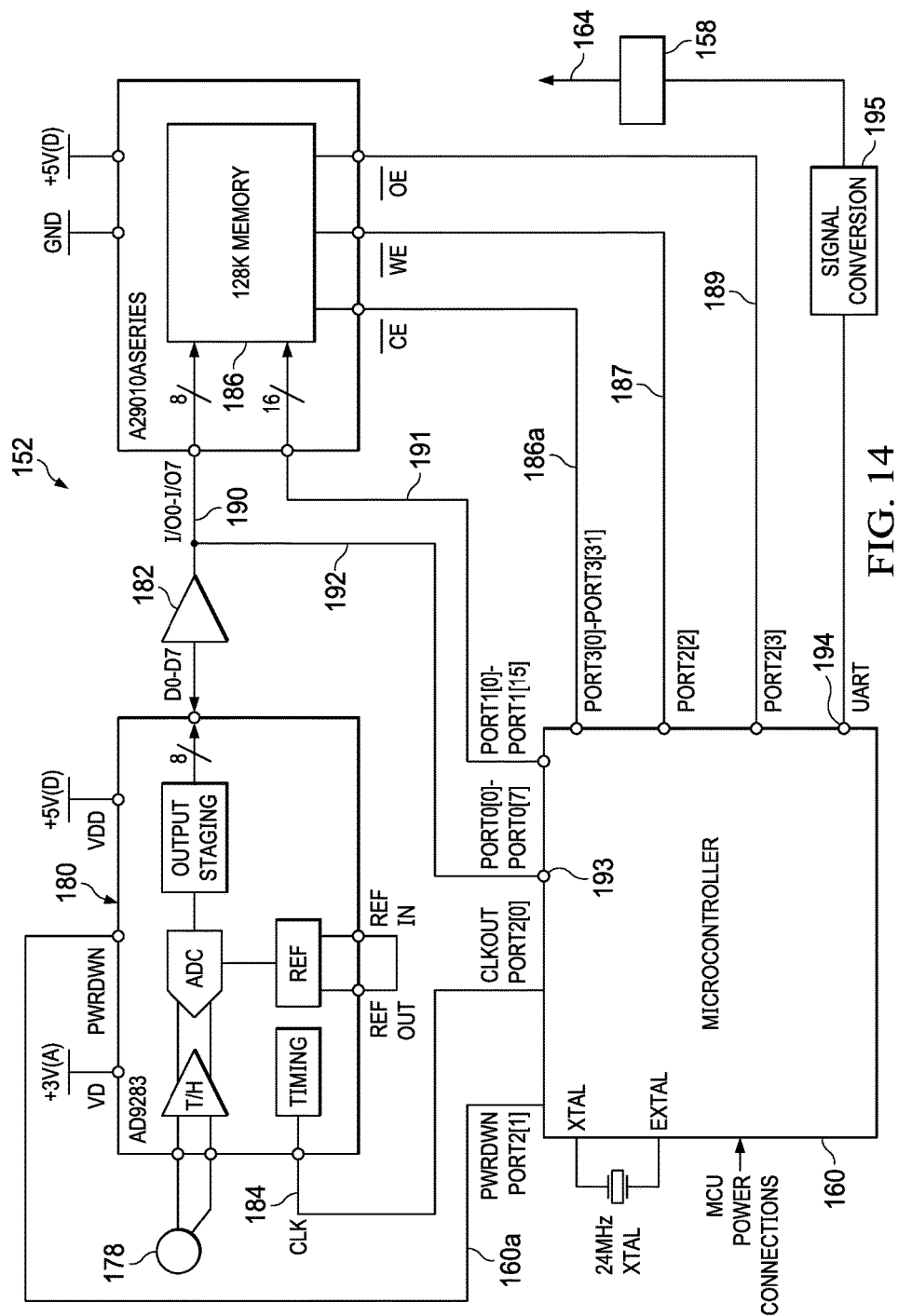
FIG. 14 is a schematic electrical circuit diagram of other portions of the processing electronics of FIG. 12.

The processing electronic circuit E includes an input signal forming circuit 150 (FIG. 13) and an output signal processing circuit 152 (FIG. 14). The input signal forming or front end circuit 150 provides pre-amplification and a switching capability which minimizes cross talk between tomography channels, and enables transmission along capacitive cables, as will be set forth. The output signal processing or back end circuit 152 converts multiple parallel analog channels of data sensed by the array U into a single serial digital data interface to minimize both the number of external feedthroughs and also the bandwidth required for transmission.

The input signal forming circuit 150 sends a pulse which is to be emitted as ultrasonic energy to the appropriate transceiver 20. The input signal forming circuit 150 also isolates the pulse emitting transceiver 20 from the output signal processing circuit 152.

The output signal processing circuit 152 amplifies the measured signals after travel through the multiphase fluid from the emitting transceiver 20 and converts the amplified measured signals into digital signals by analog to digital conversion, and stores the digital version of the measured signals in local memory. When a tomography measurement cycle by the array U is complete, the processing electronic circuit E retrieves the stored digital signals, and transmits the signal digital data in serial form to the data processing system D.

A pulse driver 154 is provided to form pulse drive signals for exciting the tomographic measurement pulses emitted by the pulse emitting transceivers. Each pulse drive signal is generated externally from processing electronic circuit E and is transmitted along a coaxial cable or transmission line 156, entering through a multipole single feedthrough 158 in outer wall 146 to connect with input signal forming circuit 150.

A digital control circuit 159, also located externally from processing electronic circuit E sends a signal to initiate a tomographic measurement sequence along a serial line 162 which enters through the same multipole feedthrough 158 to connect with the processing electronic circuit E to select one of the transceivers 20, as will be described.

Serial signal data representing the multiphase flow conditions is sent out from the processing electronic circuit E through the same multipole feedthrough 158 and thereafter passes along a coaxial cable or transmission line 164 to reach the data processing system D. The data processing system D processes the tomographic data in the manner described in Applicants' co-pending U.S. patent application Ser. No. 14/595,689 previously cited and generates a tomographic image cross section of the multiphase flow in the conduit C.

Operating electrical for the processing electronic circuit E may be supplied by an auxiliary power connection (which would be supplied through the pulse line 156 when not in use to charge up a local battery or supercapacitor) or, alternatively, a local battery.

As will be set forth, the processing electronic circuit E sends a full data set of the measured pulses to the data processing system D, rather than transmission of a single measurement indicative of the time required to reach peak amplitude sensed signal amplitude measures and held in a sample and hold circuit. The processing electronic circuit E also provides signal conversion techniques to minimize external feedthrough count.

Tomography Electronics Analog Front End or Signal Forming Circuit

Referring to FIG. 13, a four channel system for the front end or signal forming circuit 150 is shown for purposes of simplicity. As has been set forth, the present invention contemplates a channel system of sixteen or more, as well. The operating principles for the four channel system are equally applicable to any suitable number of transceivers in the array U.

The array U of four ultrasonic transceivers 20 shown in FIG. 13 are selectively driven under control of pulse drive signals from pulse driver 154 (FIG. 12) which are sent differentially from cable 156 into DIFF PULSE HI and DIFF PULSE LO connections 170a and 170b, respectively, of an analog multiplexer 170 which for the embodiment disclosed is a Model DG409DY analog multiplexer from Maxim Integrated Products.

Prior to pulsing, external digital control signals over signal line 162 from digital control circuit 159 (FIG. 12) select which of the transceivers 20 is be pulsed, the other three transceivers 20 being maintained in a listen or sense mode. The analog multiplexer 170 controls the selection.

A digital control circuit 160 (FIG. 14) performs in situ control of the processing electronics E. Digital control circuit 160 is a programmed microcontroller, functioning to perform digital control in the processing electronic circuit E, as will be described. In the disclosed embodiment, a Freescale Semiconductor MVF60NN151CKU50R ARM Cortex A5 500 MHz microprocessor is used. The digital control signal on signal line 162 selects one of a set of conductor pairs 164 on the output side of the analog multiplexer 170 according to which of the four transceivers 20 is selected to serve as pulsed energy emitting transducer.

At the same time the pulse transducer 20 selected to be energy to emit an ultrasonic energy pulse is isolated from the measurement circuits. A pair of four channels, normally closed analog switch arrays 172 which in the embodiment shown are Maxim Integrated Products Model DG411CJ switches. The analog switch arrays 172 are also controlled by the output signals from microcontroller 160. The digital control signal on line 162 causes microcontroller 160 to select the pulse transceiver 20 and opens the two switches in array 172 which connect to the low and high voltage connections to the chosen pulse transceiver. This results in the remaining three receiver transceivers 20 being connected to the measurement network. This approach significantly reduces cross talk in the system and signal to noise ratio.

Operational amplifiers 176 are provided in the form of low noise amplifiers which are used as preamplifiers so that the received signal can propagate without degradation along capacitive cables connecting to the outputs 175. In the case where a drive pulse is being sent to one of the ultrasound transceivers 20, it is necessary to isolate this signal from the amplifiers as it would otherwise introduce electrical noise into the system, because the magnitude of the drive pulse is much higher than the anticipated receiver signals. To address this, the switch arrays 172 are provided so that as the tomographic measurement is made, the single pulse sending ultrasound transmitter 20 is disconnected from the array of preamplifiers 176.

Thus, a digital signal is sent through the digital control line 162 which could be a parallel (as shown) or a serial connection, to configure the switch arrays 172, one array for the positive terminal of the ultrasound transmitter 20 and one array for the negative terminal of the same ultrasound transmitter 20.

Where a pulse is being sent to an ultrasound transmitter, the digital control signals 162 thus command the switch arrays 172 to disconnect the positive and negative terminals of that ultrasound transmitter from the measurement circuit. The other transceivers are connected with closed switches on the switching array 172 so that they can measure the transmitted acoustic signal without electrical interference from the drive pulse.

Once the switch arrays 172 are configured, the pulsing array 170 can then direct and drive the appropriate pulse using the 2 bit MUX select and enable signal 162 towards the particular ultrasound transceiver which has been disconnected from the measurement array.

The circuit 150 is thus at this time, ready to receive the pulse to be transmitted by the sending transceiver 20. The pulse from pulse drive circuit 154 propagates through the multiplexer 170 to the chosen transceiver 20. Ultrasonic energy propagates through the multiphase fluid in the flow passage 106, and signals are received by the other transceivers 20 at different times depending on transit distance and fluid properties. The signal from each of the sensing transceivers 20 passes through an assigned one of the analog switches 172, but not the massive signal which is received and sent by the pulsing transceiver 20. Once the measurement is complete, the switch array 172 is reconfigured using the digital control to isolate and connect a different configuration of transmitters and receivers, and direct the pulse sequentially through the array.

The sensed signals from the receiving transceivers 20 pass on to a series of parallel non-inverting operational amplifiers 176 configured as preamplifiers with a gain of approximately 10. The gain level is set depending on the characteristics of the received signal). The preamplification in operational amplifiers 174 boosts the low current of the outputted signal from the sensing transceivers 20 to a level strong enough to drive modestly capacitive transmission lines connected to output terminals 175 to send the data representative of flow conditions to the signal processing circuit 152 (FIG. 14).

From the foregoing, it can be seen that the analog front end circuit or input signal forming circuit 150 of the processing electronics E sends the full measured waveforms from each of the transceivers 20 with appropriate timing. The signal forming circuit 150 also amplifies the measured signals so they can drive long capacitive cables for downhole multiphase metering and tomographic purposes. Further, the signal forming circuit 150 with the switching array 172 adaptively minimizes cross talk between the pulse drive and the measuring signals.

Digital Back End Signal Processing

The data signals from output terminals 175 of signal forming circuit 150 are received in digital back end or signal processing circuit 152, which is shown in FIG. 14. FIG. 14 illustrates schematically the components of a single channel converting the analog signals obtained by the circuit in FIG. 13 and converting them into a serial digital output format. As will be set forth, the signal processing circuit 152 which converts the multiple parallel analog channels into a single serial digital data interface. This provides minimization of the number of external feedthroughs and bandwidth required for transmission to the data processing system D.

As shown, a connection 178 receives the analog output from the preamplifiers 176 shown in FIG. 13. The number of such connections 178 in signal processing circuit 152 corresponds to the number of transceivers 20 in the array U, so sixteen is an example number of them. The analog signal received at a connection 178 is fed into an analog to digital converter or ADC 180 which converts the analog signal to an eight bit parallel data signal. The eight bit parallel data signal output of ADC 180 is fed out via a buffer array 182. Again, the number of analog to digital converters 180 and buffers 182 corresponds to the number of transceivers 20.

Each sampling of the ADC 180 is set by a single clock signal over conductor 184 which is controlled and outputted by the microcontroller or digital control circuit 160. In the disclosed embodiment, the clock is set to a frequency of 24 MHz which corresponds with the same speed as the crystal connected to the XTAL and EXTAL connections of the microcontroller 160. The clock signal is a 5V square wave oscillating at a frequency of 24 MHz, meaning that a new flow data measurement is sampled at a rate of 24 MHz. The clock signal on conductor on conductor 184 is common to each of the ADC's 180. Additionally, there is a power down or PWRDWN connection over a connection 160a which when set high disables the analog to digital converters 180. Again, the PWRDWN connection 160a is common to each of the ADC's 180.

At the same time, the digital signal microcontroller 160 controls a number of memory chips 186. Again, there are as many memory chips 186 as there are transceivers 20. In the embodiment disclosed, an eight bit FLASH memory chip of suitable size, such as an AMIC A29010A Series 128K×8 bit CMOS uniform sector flash memory from AMIC Technology Corp. is shown. Each individual memory chip 186 has its own chip enable line 186a, so there are again as many chip enable lines 186a as there are transceivers 20. The chip enable line 186a is complementary so the lines to all memory chips 186 are held low so that they are all active.

A write enable functionality over a conductor 187 is common to each memory chip 186. The write enable functionality is also complementary so conductor 187 is held low so that the memory chip 186 is in a write mode. Similarly output enable functionality is provided in common over conductor 189 to each memory chip 186 as a single digital line which is also complementary, the conductor 189 held high to cause the memory chip 186 to be in write mode.

The eight bit parallel digital data passes from ADC 180 through the buffer 182 and enters an input/output or I/O buffer 190 of the memory chip 186. In parallel with this, the microcontroller 160 sends a sixteen bit parallel address digital signal over a line 191 to specify a memory address where the eight bit data should be written. Once the data has been written, the microcontroller 160 sends write enable conductor 187 high, so the data is safely stored.

On the next clock cycle on line 182, a new eight bit data point is output ready on the associated buffer of buffer array 182. The sixteen bit address increments by eight bits so that the data from the previous cycle is not overwritten. The write enable signal on line 187 goes from high to low, and the data is written to the next consecutive eight bits in memory.

This foregoing process repeats in parallel for each channel until a full digital waveform for each channel is stored within each of the memory chips 186. Typically, the measurement of ultrasonic energy received starts on the rising edge of the pulse waveform, which is likely to be a single pulse lasting ~½ the period of the frequency chosen. As an example, with 330 kHz transceivers, this is a pulse lasting 1.2-1.6 µs. Measurement times of course may vary depending on the flow passage diameter, but it is preferred to acquire multiphase flow data over a period of 100-200 µs.

At a data acquisition rate of 24 MHz, this equates to approximately 2400-4800 samples. Each sample is stored as an eight bit number which equates to 19,200-38,400 bits. This in turn equates to a memory capacity of 18.75 kb-37.5 kb per channel. For a full tomographic measurement with a sixteen channel transceiver array U, each measurement needs to be repeated sixteen times, and each channel needs to store 300 kb-600 kb of data, which indicates the required memory capacity of memory chips 186. Memory capacity requirements can as an alternative be reduced, however, if the clock speed of the clock signal on conductor 182 is reduced.

In operation, a full tomographic measurement takes place and each of the memory chips 186 contains a dataset of multiple waveforms in digital form for each of the measurements. The dataset gathered when the transceiver 20 linked to the memory chip 186 is pulsed contains null value data as the analog switch array 172 is disconnected from the amplifier circuit 176 for the pulsing or sending transceiver 20. At the end of the measurement, the microcontroller 160 sets the PWRDWN line 160a to all ADC's 180 so that there is no output on the buffers 182 and the data from the memory chips can now be gathered.

At this time, no measurement is taking place, so the timing is not critical. The microcontroller 160a now accesses each of the memory chips 186 one by one to read the data within them. In doing so, the microcontroller 160 sequentially enables each of the memory chips 186 through its chip enable line 186a. Write enable line 187 remains high so that no writing to the memory chips 186 is allowed. The microcontroller 160 sets the address of the first part of the measured data set using the sixteen bit address on line 191, and following this sets output enable on conductor 189 low so that output is allowed. The first eight bits of data are sent along a data bus 192 into an eight bit GPIO channel 193 and following this the microcontroller 160 writes the data into its own internal memory.

Once the data is stored internally, the foregoing process repeats with an updated memory address on line 191 and the next eight bits of data are sent to the internal memory within the microcontroller 160. Depending on the size of the microcontroller memory cache, it may be possible to upload the entire contents of a single memory chip 186 or it may be necessary to send data in segments. For simplicity, the foregoing description is based on the memory cache of microcontroller 160 being large enough to take the entirety of the chip memory for each channel. It should be understood that the memory can be segmented and sent in segments of appropriate compatible size.

Once the necessary data has been fed into its cache, the microcontroller 160 then codes it in a serial data transmission format out through a UART port 194 which depending on the transmission requirements can be converted into the most appropriate data format using serial conversion electronics 195. For low bandwidth long range applications, UART-RS422 format may be acceptable. If there is not sufficient bandwidth in this format to transmit the data in a useful period of time, other higher bandwidth shorter range protocols may be utilized for serial conversion. The serial data is then output through the multipole feedthrough 158 and out to the transmission line 164 which connects to the data processing system D which performs the tomographic reconstruction as described in Applicants' previously cited co-pending U.S. patent application Ser. No. 14/585,689.

The process of acquiring flow data for one channel is now repeated. This can be done either by starting from an intermediate address within the same memory chip 186 or if another memory chip 186 needs to be accessed, by disabling the first memory chip enable line 186a and enabling the next memory chip enable line (40b—assuming b denotes the second chip) and repeating the process until the cache is filled with the necessary data which can then be transmitted to the UART port 194 for transmission as described above.

The foregoing process is repeated until the data from each of the memory chips 186 has been transmitted serially through the UART port 194 to the data processing system D. The data processing system D now contains the acquired data from each of the transceivers 20 from a single tomographic measurement by array U as described in U.S. patent application Ser. No. 14/585,689 and it can now progress to reconstruct the tomographic cross section of the image of multiphase flow.

In an operating cycle, with an example of sixteen transceivers 20, denoted by 20a, 20b, 20c, . . . , 20p, for the description below according to their sequence in the operating cycle. The first pulse is sent to a first transducer 20a via the multiplexer 170, but before this the connection of transceiver 20a to the preamplifier 176 is disabled using the analog switch array 172. Signals sensed by transceivers 20b through 20p are be amplified by their respective preamplifiers 176 and converted into eight bit digital data by their associated ADC's 180 at discrete steps in time. With each update to the ADC value, the data is stored in the memory chip 186 so that a waveform lasting 100-200 µs is thus stored for each channel with approximately 2400-4800 data points. The channel for transceiver 20a is at null or 0V values for its measurement.

In an operating cycle, the second pulse is sent to the next transceiver 20b via the multiplexer 170, but before this the connection of transceiver 20b to its preamplifier 176 is disabled using the analog switch array 172. Transceivers 20a, 20c, 20d, . . . , 20p signals are amplified by the respective preamplifiers 176 and converted into eight bit digital data by the ADC's 180 at discrete steps in time. With each update to the ADC value, the acquired data is appended to the existing data within the memory chip 186 so that a second waveform lasting 100-200 µs is stored for each channel with approximately 2400-4800 data points. The channel for transceiver 20b is at null or 0V values for its measurement.

The foregoing cycle continues through each of fifteen cycles for transceivers 20a, etc. until a sixteenth pulse is sent would be sent to last transceiver 20p in the operating cycle via the multiplexer 170. Again at this time the connection of transceiver 20p to its associated preamplifier 176 is disabled using the analog switch array 172. Signals sensed by transceivers the non-transmitting transceivers 20 are amplified by the preamplifiers 176 and converted into eight bit digital data by the ADC's 180 at discrete steps in time. With each update to the ADC value, the data is appended to the existing data within the memory 186 so that a sixteenth waveform lasting 100-200 μs is stored for each channel with approximately 2400-4800 data points. The channel for transceiver 20$p$ is at null or 0V values for its measurement.

This results in a total of sixteen measurements contained in each of the sixteen memory chips 186 with one of the measurements a null reading. The null reading is useful for registration of data later on as it demonstrates explicitly which channel was pulsing.

Once the data is collected, the microcontroller 160 can segment chunks of data from the memory sequentially, which it transmits serially out of the UART port 194 in steps the size of which depends on the cache memory size of the microcontroller 160.

Data Processing System

Figure 15:
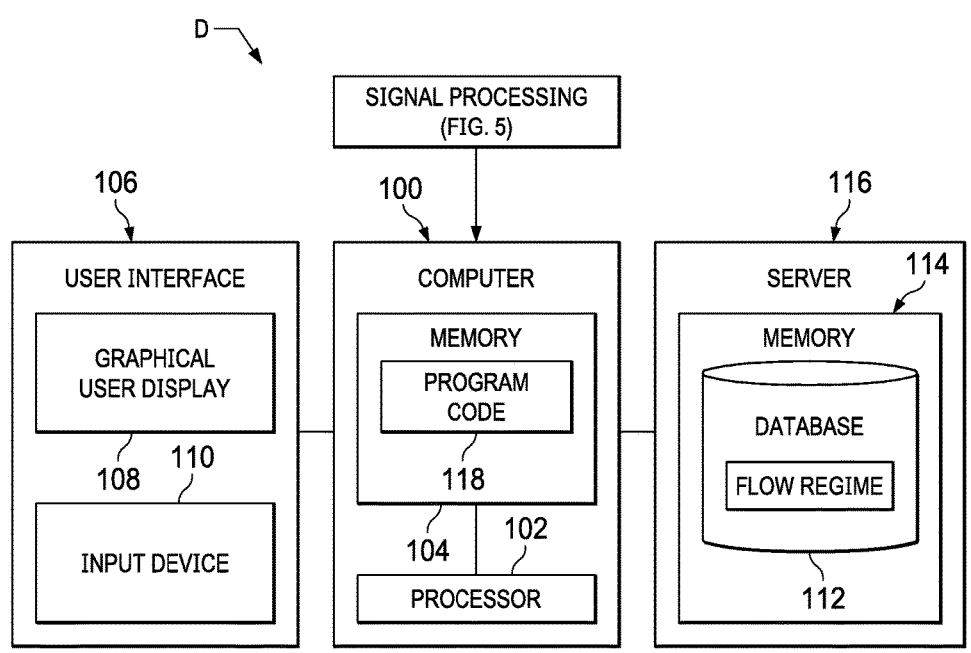
FIG. 15 is a schematic diagram of a data processing system of the processing electronics of FIG. 12.

As illustrated in FIG. 15, the data processing system D according to the present invention includes a computer 200 having a processor 202 and memory 204 coupled to the processor 202 to store operating instructions, control information and database records therein. The computer 200 may, if desired, be a Linux cluster such as is available from HP Corporation or other source, a multicore processor with nodes such as those from IBM, Intel Corporation or Advanced Micro Devices (AMD), or a mainframe computer of any conventional type of suitable processing capacity such as those available from IBM, or other source.

It should be noted that other digital processors, may be used, such as personal computers in the form of a laptop computer, notebook computer or other suitable programmed or programmable digital data processing apparatus.

The computer 200 has a user interface 206 and an output display 208 for displaying output data or records according to the present invention to measure multiphase flow based on data from the velocity/pressure measuring device 48 and form tomographic images of multiphase flow in conduits based on tomographic data from the transducer arrays U or R. The output display 208 includes components such as a printer and an output display screen capable of providing printed output information or visible displays in the form of graphs, data sheets, graphical images, data plots and the like as output records or images.

The user interface 206 of computer 200 also includes a suitable user input device or input/output control unit 210 to provide a user access to control or access information and database records and operate the computer 200. The input/output control unit 210 also may receive data measurements of flow obtained during data acquisition in the manner described above. Data processing system D further includes a database 212 stored in memory, which may be internal memory 204, or an external, networked, or non-networked memory as indicated at 214 in an associated database server 216.

The data processing system D includes program code 218 stored in non-transitory memory 204 of the computer 200. The program code 218, according to the present invention is in the form of computer operable instructions causing the data processor 202 to form tomographic images of multiphase flow in conduits, as has been set forth.

It should be noted that program code 218 may be in the form of microcode, programs, routines, or symbolic computer operable languages that provide a specific set of ordered operations that control the functioning of the data processing system D and direct its operation. The instructions of program code 218 may be stored in non-transitory form in memory 204 of the computer 200, or on computer diskette, magnetic tape, conventional hard disk drive, electronic read-only memory, optical storage device, or other appropriate data storage device having a non-transitory computer usable medium stored thereon. Program code 218 may also be contained on a data storage device such as server 214 as a non-transitory computer readable medium, as shown.

The invention has been sufficiently described so that a person with average knowledge in the matter may reproduce and obtain the results mentioned in the invention herein Nonetheless, any skilled person in the field of technique, subject of the invention herein, may carry out modifications not described in the request herein, to apply these modifications to a determined structure, or in the manufacturing process of the same, requires the claimed matter in the following claims; such structures shall be covered within the scope of the invention.

It should be noted and understood that there can be improvements and modifications made of the present invention described in detail above without departing from the spirit or scope of the invention as set forth in the accompanying claims.

The invention claimed is:

1. An apparatus for telemetry of analog measured ultrasonic signals to form a measure of cross sectional composition of a three phase oil, gas and water mixture in multiphase flow within a conduit for tomographic imaging of the oil, gas and water in the mixture, comprising:
    (a) a digital control circuit sending a control signal to initiate a tomographic measurement sequence of ultrasonic energy signal pulses;
    (b) an array of a plurality of ultrasonic transceivers mounted about the periphery of the conduit transmitting ultrasonic energy signal pulses of the tomographic measurement sequence for travel through the mixture in multiphase flow in the conduit;
    (c) the array of a plurality of ultrasonic transceivers mounted about the periphery of the conduit further receiving ultrasonic energy signals after travel through the mixture in multiphase flow in the conduit;
    (d) a pulse driver forming pulse drive signals to cause travel of ultrasonic energy signal pulses of the tomographic measurement sequence through the mixture in multiphase flow in the conduit;
    (e) an input signal forming circuit sending a pulse to be emitted as ultrasonic energy during the tomographic measurement sequence to a selected one of the plurality of ultrasonic transceivers for travel through the mixture in multiphase flow in the conduit;
    (f) the input signal forming circuit including a multiplexer responding to the control signal from the digital control circuit to isolate the selected one of the plurality of ultrasonic transceivers during emission of a pulse of ultrasonic energy;
    (g) the input signal forming circuit multiplexer further responding to the control signal to enable assigned ones of the plurality of ultrasonic transceivers to receive measures of the emitted pulse of ultrasonic energy after travel through the mixture in multiphase flow between the transceivers;
    (h) an output signal processing circuit receiving measures of the ultrasonic energy from the enabled assigned ones of the of the plurality of ultrasonic transceivers;
    (i) a plurality of analog switches responsive to the input signal forming circuit multiplexer to receive measures of the ultrasonic energy from the enabled assigned ones of the plurality of ultrasonic transceivers;

(j) the output signal processing circuit further including an analog to digital converter converting the received measures of the ultrasonic energy signals from the plurality of analog switches into digital data signals; and (k) the output signal processing circuit further transferring the digital data signals for processing to determine the cross sectional composition of the oil, gas and water mixture in multiphase flow in the conduit.

2. The apparatus of claim 1, further including:
amplifiers receiving and amplifying the ultrasonic energy signals for processing by the output signal processing circuit.

3. The apparatus of claim 1, wherein the input signal forming circuit multiplexer isolates the selected one of the plurality of ultrasonic transceivers from receiving ultrasonic energy signals after travel through the mixture in multiphase flow in the conduit.

4. The apparatus of claim 1, wherein the analog switches comprise analog switches receiving measures of attenuation of the ultrasonic energy of the individually emitted ultrasonic energy signals from assigned ones of the plurality of ultrasonic transceivers after travel through the mixture in multiphase flow between the transceivers.

5. The apparatus of claim 1, further including:
the output signal processing circuit further forming the digital data signals in parallel format.

6. The apparatus of claim 5, further including:
a format converter transforming the parallel format digital data signals into serial format digital data signals.

7. The apparatus of claim 6, further including:
the digital control circuit further controlling operation of output signal processing circuit.

8. An apparatus for forming a tomographic image of cross sectional composition of a three phase oil, gas and water mixture in multiphase flow within a conduit, comprising:

(a) a digital control circuit sending a control signal to initiate a tomographic measurement sequence of ultrasonic energy signal pulses;

(b) an array of a plurality of ultrasonic transceivers mounted about the periphery of the conduit transmitting ultrasonic energy signal pulses of the tomographic measurement sequence for travel through the mixture in multiphase flow in the conduit;

(c) the array of a plurality of ultrasonic transceivers mounted about the periphery of the conduit further receiving ultrasonic energy signals after travel through the mixture in multiphase flow in the conduit;

(d) a pulse driver forming pulse drive signals to cause travel of ultrasonic energy signal pulses of the tomographic measurement sequence through the mixture in multiphase flow in the conduit;

(e) an input signal forming circuit sending a pulse to be emitted as ultrasonic energy during the tomographic measurement sequence to a selected one of the plurality of ultrasonic transceivers for travel through the mixture in multiphase flow in the conduit;

(f) the input signal forming circuit including a multiplexer responding to the control signal from the digital control circuit to isolate the selected one of the plurality of ultrasonic transceivers during emission of a pulse of ultrasonic energy;

(g) the input signal forming circuit multiplexer further responding to the control signal to enable assigned ones of the plurality of ultrasonic transceivers to receive measures of the emitted pulse of ultrasonic energy after travel through the mixture in multiphase flow between the transceivers;

(h) an output signal processing circuit receiving measures of the ultrasonic energy from the enabled assigned ones of the of the plurality of ultrasonic transceivers;

(i) a plurality of analog switches responsive to the input signal forming circuit multiplexer to receive measures of the ultrasonic energy from the enabled assigned ones of the plurality of ultrasonic transceivers;

(j) the output signal processing circuit further including an analog to digital converter converting the received measures of the ultrasonic energy signals from the plurality of analog switches into digital data signals; and (k) the output signal processing circuit further transferring the digital data signals for processing to determine the cross sectional composition of the oil, gas and water mixture in multiphase flow in the conduit: and (l) a data processing system forming the tomographic image of the cross sectional composition of the three phase oil, gas and water mixture in multiphase flow within the conduit from the transferred digital data signals.

* * * * *